(12) United States Patent
Dumas et al.

(10) Patent No.: US 10,900,699 B2
(45) Date of Patent: Jan. 26, 2021

(54) HELIUM MANAGEMENT CONTROL SYSTEM

(71) Applicant: Edwards Vacuum LLC, Sanborn, NY (US)

(72) Inventors: Oliver J. Dumas, East Sandwich, MA (US); Maureen C. Buonpane, Mansfield, MA (US); Doreen J. Ball-DiFazio, Hopkinton, MA (US); Ronald N. Morris, Bedford, MA (US); Allen J. Bartlett, New London, NH (US); Leonard A. Loranger, Medfield, MA (US); Joseph Chopy, Jr., Cumberland, RI (US); Robert P. Sullivan, Wilmington, MA (US); John J. Varone, Seekonk, MA (US); Paul E. Amundsen, Ipswich, MA (US)

(73) Assignee: Edwards Vacuum LLC, Sanborn, NY (US)

( * ) Notice: Subject to any disclaimer, the term of this patent is extended or adjusted under 35 U.S.C. 154(b) by 122 days.

(21) Appl. No.: 16/173,623

(22) Filed: Oct. 29, 2018

(65) Prior Publication Data
US 2019/0063807 A1 Feb. 28, 2019

Related U.S. Application Data

(62) Division of application No. 14/001,803, filed as application No. PCT/US2012/027755 on Mar. 5, 2012, now Pat. No. 10,113,781.
(Continued)

(51) Int. Cl.
F25B 49/02 (2006.01)
F25J 1/02 (2006.01)
(Continued)

(52) U.S. Cl.
CPC ............ *F25B 49/022* (2013.01); *A01N 63/10* (2020.01); *F25B 9/00* (2013.01); *F25J 1/0065* (2013.01);
(Continued)

(58) Field of Classification Search
CPC ........ F25J 1/0294; F25J 1/0298; F25J 1/0065; F25J 1/0245; F25J 2270/912;
(Continued)

(56) References Cited

U.S. PATENT DOCUMENTS 4,535,602 A * 8/1985 Alsenz ................. F25B 49/022
                                                          236/1 EA
4,555,907 A 12/1985 Bartlett
(Continued)

FOREIGN PATENT DOCUMENTS

| CN | 100406815 C | 1/2005 |
|----|-------------|--------|
| CN | 1926389 A | 3/2007 |

(Continued)

OTHER PUBLICATIONS

Notification of Transmittal of the International Search Report and the Written Opinion of the International Searching Authority, or the Declaration for PCT/2012/027755, entitled "Helium Management Control System", dated Jan. 17, 2013.
(Continued)

*Primary Examiner* — Kun Kai Ma
(74) *Attorney, Agent, or Firm* — Theodore M. Magee; Westman, Champlin & Koehler, P.A

(57) ABSTRACT

A refrigerant management system controls the supply of refrigerant from two or more variable speed and fixed speed compressors to a plurality of cryogenic refrigerators. The system employs a plurality of sensors to monitor and regulate the overall refrigerant supply to deliver an appropriate refrigerant supply to each of the cryogenic refrigerators. The
(Continued)

amount of refrigerant to supply is based on an aggregate demand for refrigerant from the plurality of cryogenic refrigerators and a refrigerant correction metric. An appropriate supply of refrigerant is distributed to each cryogenic refrigerator by adjusting the speed of the variable speed compressors or, alternatively, selectively turning the compressors on or off. The speed of the variable speed compressors is adjusted by determining an amount of refrigerant to supply to the plurality of cryogenic refrigerators. If the aggregate demand for refrigerant exceeds the capacity of the compressors, then the speed of a refrigerator within the plurality of refrigerators is adjusted.

18 Claims, 11 Drawing Sheets

Related U.S. Application Data

(60) Provisional application No. 61/449,502, filed on Mar. 4, 2011.

(51) Int. Cl.
 *F25B 9/00* (2006.01)
 *F25J 1/00* (2006.01)
 *A01N 63/10* (2020.01)
 *G01N 33/50* (2006.01)

(52) U.S. Cl.
 CPC ........... *F25J 1/0245* (2013.01); *F25J 1/0269* (2013.01); *F25J 1/0294* (2013.01); *F25J 1/0298* (2013.01); *G01N 33/5085* (2013.01); *F25J 2270/912* (2013.01)

(58) Field of Classification Search
 CPC .......... F25B 2400/04; F25B 2700/1933; F25B 2700/1931; F25B 2700/21156
 See application file for complete search history.

(56) References Cited

U.S. PATENT DOCUMENTS

| | | | |
|---|---|---|---|
| 4,589,263 A | 5/1986 | DiCarlo et al. | |
| 5,010,737 A * | 4/1991 | Okumura | F25B 9/10 62/55.5 |
| 5,211,022 A | 5/1993 | Bartlett et al. | |
| 5,375,424 A * | 12/1994 | Bartlett | F04B 37/08 417/901 |
| 5,483,803 A | 1/1996 | Matte et al. | |
| 5,517,823 A * | 5/1996 | Andeen | F04B 37/085 62/55.5 |
| 5,775,109 A | 7/1998 | Eacobacci, Jr. et al. | |
| 5,862,671 A | 1/1999 | Lessard et al. | |
| 5,887,438 A | 3/1999 | Johnson et al. | |
| 6,216,467 B1 * | 4/2001 | O'Neil | F25B 9/14 62/6 |
| 6,330,804 B1 | 12/2001 | Uno et al. | |
| 6,529,590 B1 * | 3/2003 | Centers | F04B 49/065 379/106.01 |
| 7,127,901 B2 | 10/2006 | Dresens et al. | |
| 7,555,911 B2 * | 7/2009 | Tanaka | F04B 37/08 62/228.1 |
| 7,788,942 B2 | 9/2010 | Dresens et al. | |
| 10,113,781 B2 | 10/2018 | Dumas et al. | |
| 2002/0020178 A1 | 2/2002 | Uno et al. | |
| 2003/0014985 A1 * | 1/2003 | Dresens | F04B 37/08 62/149 |
| 2003/0024252 A1 * | 2/2003 | Funayama | B01D 8/00 62/55.5 |
| 2005/0244277 A1 * | 11/2005 | Hurst, Jr. | F25B 49/022 417/216 |
| 2005/0262852 A1 | 12/2005 | Amundsen et al. | |
| 2006/0293816 A1 | 12/2006 | Li | |
| 2008/0175717 A1 | 7/2008 | Schnetzka et al. | |
| 2008/0307813 A1 | 12/2008 | Lifson et al. | |
| 2009/0019886 A1 | 1/2009 | Kotani et al. | |
| 2010/0065245 A1 | 3/2010 | Imada et al. | |
| 2010/0107659 A1 | 5/2010 | Hildreth, Jr. | |
| 2010/0186433 A1 | 7/2010 | Galante et al. | |
| 2010/0266920 A1 | 10/2010 | Kanie et al. | |
| 2011/0008181 A1 | 1/2011 | Hurst, Jr. et al. | |
| 2011/0016891 A1 * | 1/2011 | McDonald | G05B 9/02 62/55.5 |
| 2011/0126554 A1 | 6/2011 | Morris et al. | |
| 2014/0130527 A1 | 5/2014 | Dumas et al. | |
| 2014/0260378 A1 | 9/2014 | Gomes et al. | |

FOREIGN PATENT DOCUMENTS

| | | |
|---|---|---|
| EP | 1 443 286 A1 | 8/2004 |
| EP | 1 985 939 A1 | 10/2008 |
| EP | 2 233 862 A2 | 9/2010 |
| GB | 2 273 763 A | 6/1994 |
| GB | 2 380 248 A | 4/2003 |
| JP | 60-194259 U | 12/1985 |
| JP | 5-18617 A | 1/1993 |
| JP | H0518617 A | 1/1993 |
| JP | 6-507958 A | 9/1994 |
| JP | H7-190576 A | 7/1995 |
| JP | H8-178438 A | 7/1996 |
| JP | H10-153179 A | 6/1998 |
| JP | 2000-257964 A | 9/2000 |
| JP | 2000-512703 A | 9/2000 |
| JP | 2001-147269 A | 5/2001 |
| JP | 2001-302082 A | 10/2001 |
| JP | 2003-113779 A | 4/2003 |
| JP | 2003113779 A | 4/2003 |
| JP | 2004-085048 A | 3/2004 |
| JP | 2006-046681 A | 2/2006 |
| JP | 2007-190576 A | 8/2007 |
| JP | 2007-218438 A | 8/2007 |
| JP | 2008-014599 A | 1/2008 |
| JP | 2008-178438 A | 8/2008 |
| JP | 2010-223477 A | 10/2010 |
| WO | 2009/028450 A1 | 3/2009 |
| WO | 2009028450 A1 | 3/2009 |

OTHER PUBLICATIONS

Notification Concerning Transmittal of International Preliminary Report on Patentability and Written Opinion for PCT/US2012/027755 entitled "Helium Management Control System", dated Sep. 19, 2013.
PCT International Search Report dated Jan. 17, 2013 for corresponding PCT application Serial No. PCT/US2012/027755.
PCT International Preliminary Report on Patentability and Written Opinion dated Jan. 17, 2013 for corresponding PCT application Serial No. PCT/US201/027755.
Prosecution history of corresponding U.S. Appl. No. 14/001,803 including: Office Action dated Aug. 1, 2016, Amendment dated Jan. 31, 2017, Final Office Action dated Jun. 26, 2017, Amendment After Final Rejection dated Sep. 25, 2017, Advisory Action dated Oct. 17, 2017 and Notice of Allowance dated Jun. 20, 2018.
Japanese Office Action dated May 2, 2020 for corresponding Japanese application Serial No. JP2019060809.

\* cited by examiner

| Location | Requested Flow SCFM, F1 F2 | Actual Flow SCFM |
|---|---|---|
| A | SCFMmax, F1=F2=Fmax | SCFMmax |
| B | SCFMmin, F1=F2=35Hz | SCFMmin |
| C (increasing SCFM) | SCFMmax/2, F1=Fmax, F2=0 | SCFMmin |
| C (decreasing SCFM) | SCFMmax/2 - Hysteresis | SCFMmin |
| D (increasing SCFM) | SCFMmax/2, F1=Fmax, F2=0 | SCFMmax/2 |
| D (increasing SCFM) | SCFMmax/2 - Hysteresis | SCFMmax/2 - m*Hysteresis |
| E | SCFMmin/2, F1=35Hz, F2=0 | SCFMmin/2 |
| F | 0 | SCFMmin/2 |

Where SCFMmax = max SCFM capacity (f = Fmax) with two motors running
SCFMmin = min SCFM capacity (f = 35Hz) with two motors running

FIG. 5D

HELIUM MANAGEMENT CONTROL SYSTEM

RELATED APPLICATION(S)

This application is a divisional of U.S. application Ser. No. 14/001,803, filed Jan. 9, 2014, which is the U.S. National Stage of International Application No. PCT/US2012/027755, filed on Mar. 5, 2012, published in English, which claims the benefit of U.S. Provisional Application No. 61/449,502, filed on Mar. 4, 2011. The entire teachings of the above applications are incorporated herein by reference.

BACKGROUND

Vacuum process chambers are often employed in manufacturing to provide a vacuum environment for tasks such as semiconductor wafer fabrication, deposition processes, electron microscopy, gas chromatography, and others. Such chambers are typically achieved by attaching a vacuum pump to the vacuum process chamber in a sealed arrangement. The vacuum pump operates to remove substantially all of the molecules from the vacuum process chamber, therefore creating a vacuum environment.

One type of vacuum pump is a cryopump, such as that disclosed in U.S. Pat. No. 5,862,671, issued Jan. 26, 1999, assigned to the assignee of the present application and incorporated by reference in its entirety. Cryopumps remove molecules from a vacuum process chamber by cooling a surface to temperatures approaching absolute zero. At such temperatures, gases condense or are adsorbed on the cooled surface, called a cryogenic array, thereby removing molecules from the vacuum process chamber.

Other types of cryopumps are designed to operate at temperatures greater than absolute zero. These cryopumps remove specific gases from a chamber such as water, hydrocarbons, process by-products, outgas species and process gases. Waterpumps as described on U.S. Pat. No. 5,483,803 is an example of one of such cryopumps. Other cryopumps such as that disclosed in U.S. Pat. No. 5,211,022 do not to remove all gases but maintain a low pressure of a process gas in a vacuum chamber.

Cryopumps typically employ a refrigerator to achieve the cryogenic temperatures required. The type of refrigerator required depends on the temperature required for the species being pumped and other parameters such as heat load and vibration. Typically, Stirling, Gifford-McMahon, and pulse tube refrigerators are used for cryogenic vacuum pumps. These refrigerators require a supply of compressed gas from a compressor to supply a flow of refrigerant to the cryogenic refrigerator in the cryopump. Cryopumps that require temperatures near absolute zero use helium as the compressed gas. A cryogenic array is in thermal communication with the cold end of the refrigerator and cooled therewith. Inside the refrigerator a displacer, driven by a displacer drive which reciprocates the displacer, regulates the quantity of helium used. Expansion of refrigerant gas, such as helium, in the refrigerator creates cooling and heat is drawn off the cryogenic array, generating the cryogenic temperatures required to condense gases on the cryogenic array.

Alternatively, pulse tube displacers do not move, but, rather, use a pressure wave instead. Although cryopumps have been described with motor driven designs, cryopumps may be designed with pneumatic driven systems.

The amount of helium refrigerant available to the cryogenic refrigerator determines the rate at which cooling occurs. A greater supply of helium enables the refrigerator to consume more helium which produces more refrigeration. It decreases the amount of time required for cool down, which is the time required to achieve cryopumping temperatures, and at operating temperatures enables the refrigerator to produce more refrigeration when demanded by the varying process conditions in the vacuum chamber. A greater supply of helium also enables the refrigerator to increase consumption to maintain refrigeration capacity as normal degradation of the refrigerator efficiency occurs during refrigerator operating life. The rate of helium consumption also varies with the temperature of the cryogenic refrigerator. As the cryogenic refrigerator becomes colder, a greater supply of helium is required to continue the cooling process. In a cryopumped vacuum process chamber, downtime can result in substantial economic impact, due to lost manufacturing time. Accordingly, the capability to rapidly achieve and maintain cryopumping temperatures is beneficial.

One prior art type of helium distribution is described in U.S. Pat. No. 5,775,109, entitled "Enhanced Cooldown of Multiple Cryogenic Refrigerators Supplied by a Common Compressor," filed Jan. 2, 1997 and assigned to the assignee of the present application, incorporated herein by reference in its entirety. This patent suggests individually monitoring the temperature of each of a plurality of cryopumps to control the speed of each displacer drive motor when a cryopump attains a triggering temperature. As the refrigerators in cryopumps require varying amounts of helium depending upon the operation currently being performed, regulating the drive motor speed can reduce or increase the helium supply accordingly. In this system, each cryopump monitors temperature and controls the drive motor speed accordingly.

Frequently, however, a common helium supply manifold supplying a plurality of cryopumps is capable of supplying more helium than required by all of the cryopumps. Excess helium which is not required by the refrigerators to maintain adequate refrigeration can waste power and other resources required to maintain the helium refrigerant supply. Conversely, insufficient helium will result in inadequate refrigeration by the refrigerators and, potentially, loss of vacuum performance by cryopumps.

It should be noted that the aforementioned problems apply to cryogenic refrigerators as well as cryopumps. These refrigerators may be used in a wide variety of cooling applications including but not limited to high temperature superconductors (HTS), semiconductor manufacturing, processing and storage of biological samples, MRI imaging, and instrumentation cooling.

SUMMARY

Provided here is a technique and system for supplying amount of refrigerant gas needed by refrigerators to achieve the required cooling conditions.

A method and corresponding refrigeration system relate to controlling supply of a refrigerant. A compressor is configured to supply a refrigerant through a high pressure supply line, and the refrigerant is returned to the compressor through a low pressure return line. A plurality of refrigerators are coupled to the compressor to receive refrigerant from the supply line and return refrigerant to the return line. Further, an electronic controller is configured to obtain an aggregated demand for the refrigerant based on communications from the plurality of refrigerators. The electronic controller is further configured to control speed of the compressor based on the aggregate demand for the refrigerant corrected by a refrigerant correction metric.

The compressor may be one of a plurality of variable speed compressors or combination of variable speed and fixed speed compressors. The electronic controller may be further configured to control the speed of the compressor based on one or more of a return pressure from the low pressure return line, supply pressure feedback loop from the high pressure supply line, and a pressure differential between a supply pressure and return pressure. Additionally, the electronic controller may be further configured to determine whether to increase or decrease a supply of refrigerant and to notify a return pressure setpoint calculator of the increase or decrease in the aggregated demand. The electronic controller may be one or more controller units configured to operate together, where some functions are in one controller and other functions are in another controller.

The return pressure setpoint calculator may be configured to determine a return pressure setpoint based on the determination to increase or decrease the supply of refrigerant. A refrigerant supply correction controller may be configured to determine an error between the return pressure setpoint and the return pressure. Further, the refrigerant supply correction controller further may be configured to calculate a refrigerant supply correction based on the error between the return pressure setpoint and the return pressure. The refrigerant supply correction controller may also be configured to determine an amount of refrigerant to supply to the plurality refrigerators based on a comparison of the refrigerant supply correction and the aggregate demand for the refrigerant from the plurality of refrigerators.

Alternatively, the refrigerators may not demand flow but only consume refrigerant to meet refrigeration needs, while a main controller monitors operating variables of the refrigerators to determine the flow of refrigerant the refrigerators require.

The compressor may be one of a plurality of variable speed compressors. A compressor motor controller may be configured to turn a subset of the plurality of variable speed compressors on or off based on the determined amount of refrigerant to supply to the plurality of refrigerators. The compressor motor controller may further be configured to determine the speeds of the subset of the plurality of variable speed compressors turned on as a function of the determined amount of refrigerant to supply to the plurality of refrigerators and the subset of the plurality of variable speed compressors turned on and also to send a command to the subset of the plurality of variable speed compressors turned on to run at the determined speeds. For example, there may be multiple variable speed compressors running at different speeds to meet demand. Also, there may be fixed speed compressors running on the system and a subset of the fixed speed compressors may be turned on or off to meet refrigerant demand.

The electronic controller may also be configured to determine whether the compressor is able to supply the plurality of refrigerators with the aggregated demand for refrigerant. If the compressor is unable to supply the plurality of refrigerators with the aggregated demand for refrigerant, the controller may adjust a speed of a refrigerator within the plurality refrigerators or reduce the allocation of refrigerant to the refrigerators wherein the controls in the refrigerators adjust the speed of the refrigerator.

Additionally, the electronic controller may be configured to obtain an aggregate demand for refrigerant from a plurality of cryogenic refrigerators. Further, the cryogenic refrigerators may be included in cryopumps.

A method for controlling supply of a refrigerant comprises at a controller, obtaining an aggregated demand for a refrigerant based on communications from plural refrigerators. With the controller, the method controls speed of a compressor that delivers refrigerant to the plural refrigerators based on the aggregated demand for the refrigerant.

A refrigeration system for controlling supply of a refrigerant comprises plural variable speed compressors including a high pressure supply line and a low pressure return line. The plural variable speed compressors are configured to supply a refrigerant to plural refrigerators. A compressor controller selectively turns a subset of the plural variable speed compressors on or off based on a requirement of refrigerant.

The plural compressors may comprise only two variable speed compressors. If a fault condition exists in either of the two variable speed compressors, the compressor control system may adjust the speed of the variable speed compressor without a fault condition to a maximum motor speed.

Further, if both of the two variable speed compressors are on, the compressor controller may be configured to determine whether to switch to a single variable speed compressor operational state from a dual variable speed compressor operational state. The compressor controller may further be configured to calculate an amount of refrigerant to supply to the plural refrigerators. If the calculated amount of refrigerant to supply to the plural refrigerators is less than a threshold refrigerant output of a single compressor, the compressor controller may select and turn one of the two variable speed compressors off.

Additionally, the compressor controller may turn one of the two variable speed compressors off after increasing the speed of the variable speed compressor that is to be left on to a speed capable of delivering the calculated amount of refrigerant to the plural refrigerators. The compressor controller may further be configured to turn one of the two variable speed compressors off if the calculated amount of refrigerant to supply to the plural refrigerators is less than the threshold refrigerant output of the single compressor for a period of time.

The compressor controller may select one of the two variable speed compressors to turn off based on a history of turn offs. The compressor controller may also be configured to determine if the differential between the supply pressure and the return pressure collapses by more than a predetermined threshold. If the differential pressure collapses by more than the predetermined threshold, the compressor controller may switch from the single variable speed compressor operational state to a dual variable speed compressor operational state.

Further, if one of the dual variable speed compressors is off, the compressor controller may be configured to calculate an amount of refrigerant to supply to the plural refrigerators. Additionally, if the calculated amount of refrigerant to supply to the plural refrigerators is greater than a threshold refrigerant output of a single compressor, the compressor controller may switch to the dual variable speed compressor operational state.

The compressor controller may be configured to switch to the dual variable speed compressor operational state and turn one of the two variable speed compressors on if the calculated amount of refrigerant to supply to the plural refrigerators is greater than the threshold refrigerant output of a single compressor for a period of time.

The compressor controller may switch to the dual variable speed operational state and adjust the speed of the two variable speed compressors to supply the total refrigerant aggregate demand to the refrigerators.

The compressor controller, in switching to the dual variable speed operational state, may increase the speed of the variable speed compressor being turned on prior to decreasing the speed of the variable speed compressor active during the single variable speed operational state.

A method for controlling supply of a refrigerant comprises supplying refrigerant from plural variable speed compressors to plural refrigerators and selectively turning a subset of the plural compressors on or off based on a requirement of refrigerant.

A refrigerant system for controlling supply of a refrigerant comprises separate variable speed compressors. Additionally, the refrigerant system may comprise separate variable speed compressors with a separate fixed speed compressor. Alternatively, two or more compressor pumps may be configured within a single compressor structure where at least one of the pumps is variable speed and each pump is controlled as though it was a separate compressor.

In one embodiment according to the invention, there is provided a method for diagnosing a vacuum performance characteristic of a vacuum component. The method comprises automatically detecting an electronic signal based on a vacuum performance characteristic of the vacuum component during operation of the vacuum component, and automatically communicating a data record based on the detected electronic signal over a data network in communication with the vacuum component during operation of the vacuum component. The vacuum performance characteristic is automatically diagnosed based on the communicated data record. The vacuum component may be a cryogenic vacuum pump, a compressor, a turbomolecular pump, a roughing pump, a water pump, a chiller, a valve, a gauge or another vacuum component. The data record may include a time stamp based on a time associated with the detected electronic signal.

In related embodiments, the detected electronic signal may be a signal based on an increase in a refrigerator motor speed of a cryogenic vacuum pump. Automatically detecting the electronic signal may include detecting the increase in the refrigerator motor speed, detecting an increase in a temperature of a refrigerator stage of the cryogenic vacuum pump prior to the increase in the refrigerator motor speed, and detecting lack of operation of a heater for the refrigerator stage while the increase in the temperature of the refrigerator stage occurred.

A method and corresponding refrigeration system relate to controlling supply of a refrigerant. A controller detects a fault in a refrigerant system including at least one compressor, where the at least one compressor is any combination of fixed speed and variable speed compressors. Upon detecting the fault, the controller initiates fault recovery procedures.

The controller may further be configured to detect a communication loss between elements of the refrigerant system. Upon determining the communication loss, the controller increases a speed of the at least one compressor. If the detected fault indicates that a current exceeds a predetermined threshold, the controller may issue a warning signal and gradually reduce a speed of the at least one compressor. If the current continues to exceed the predetermined threshold and the speed of the at least one compressor is at a minimum threshold, the controller turns off the at least one compressor.

The controller may also override a speed control algorithm when a fault exists and reduction in compressor speed is used to recover from the fault. When the compressor motor speed is reduced to clear the fault, the pressure differential or difference between the pressures in the supply and return lines is allowed go below the setpoint used for speed control. The fault recovery process to clear the fault will take precedence over the normal control to maintain a defined pressure differential. In addition, the controller may further determine whether a motor has reached a temperature greater than a maximum temperature threshold, and if the temperature is greater than the threshold, the controller is configured to reduce a speed of the motor until a minimum speed threshold is reached, if necessary. In addition, the controller may turn off the motor if the motor remains at the temperature greater than the maximum threshold.

Also, the controller is further configured to determine whether a drive transistor such as an insulated gate bipolar transistor (IGBT) has reached a temperature greater than a maximum threshold and if the temperature is greater than the threshold, the controller reduces a speed of a compressor associated with the drive transistor until a minimum speed threshold is reached. The controller may also turn off the compressor if the drive transistor remains at the temperature greater than the maximum threshold.

The controller may also determine whether an inlet or outlet water temperature exceeds a threshold, and if the temperature exceeds the threshold, the controller issues a warning. Further, the controller determines whether a temperature of at least one heat exchanger exceeds a temperature threshold, and if the temperature exceeds the temperature threshold, the controller issues a warning. The controller is also configured to turn off a compressor associated with the at least one heat exchanger.

If an internal ambient temperature of an area including electronics is greater than a threshold temperature, the controller issues a warning. Further, in another embodiment, more than one compressor may share a helium circuit. In such a scenario, if a pressure differential falls below a threshold at a point in time when one of the compressors in the helium circuit is turned off, the controller turns the compressor back on, a check valve fault warning is issued and the controller will not turn the compressor off as part of the normal refrigerant control process until the unit is repaired.

In response to detecting a loss or fault of a pressure sensor or a loss of communications to or from the sensor, the controller issues a warning of the fault and runs the compressors at maximum speed. Additionally, the controller is configured to determine whether a pressure differential metric is below a threshold value and if the value is below the threshold, the controller sets compressors to a maximum speed.

The controller may also reduce allocation of refrigerant to refrigerators if the pressure differential metric remains below the threshold value for a predetermined amount of time. In response to detecting an invalid pressure sensor, the controller may set compressors to a maximum speed. The controller may also issue a warning in response to detecting a fan failure.

In response to detecting a differential pressure or difference between a pressure supply and pressure return to be below a threshold value, the controller may check a refrigerator temperature to determine if the refrigerator is maintaining a specific temperature. If the refrigerator is maintaining the specific temperature, the controller determines that a fault in a pressure sensor has occurred and sets compressors to a maximum speed.

Further, the controller may utilize at least one working pressure sensor of a plurality of pressure sensors as a sensor feedback if more than one of the plurality of pressure sensors is measuring a high pressure supply line and a fault is detected in a subset of the pressure sensors. Alternative, if more than one of the pressure sensors is measuring a low pressure return line and a fault is detected in a subset of the sensors, the controller may utilize at least one working sensor as a sensor input to a control system.

If a compressor is shut off in response to a detected fault, the controller may turn the compressor back on and allow the system to operate under normal control. If the compressor shuts down again in response to a detected fault, a warning is issued and the compressor will be allowed to come back on and to operate again. After a predetermined number of shutdowns within a predetermined time period, the compressor will not be allowed to restart and a warning is issued.

In other words, if there is a problem and a fault recovery remedy, such as slowing down the compressor, fails to remedy the fault, the controller shuts off the compressor and then restarts the compressor. This restart sequence may be repeated. For instance, the controller may shut down the compressor if the shut down and turn on sequence (e.g., reboot) fails to remedy the fault. This may be repeated up to three times in within a set time. If the fault is not remedied, then the compressor remains off. Warnings for any type of fault may be stored internal to the compressor, displayed at the compressor, communicated to a controller for the refrigerator system, communicated to the host tool, and/or communicated to any other system monitoring the tool or refrigeration system.

Thermostatic valves placed in a cooling water circuit at the outlet of the compressor or group of compressors or in the individual cooling circuits within the compressor may reduce the total cooling water flow by the devices. The temperature setpoint of the valves will maintain the items being cooled at safe levels for performance and reliability. These valves may be place in circuits for cooling counter-flow heat exchangers for cooling fluids such as the refrigerants and lubricating fluid as well as heat exchangers attached to the compressor pump and electronics cooling plates. Additionally, the use of thermostatic valves on the entrance or exit to electronics cooling plates is to maintain the cooling plate for the electronics above a threshold to prevent condensation. Thermally isolated thermostatic flow control valves may be coupled to the cooling water circuit to adjust flow around a temperature setpoint, thereby maintaining a minimum amount of cooling water necessary to maintain motor winding temperatures within operating specifications.

The controller may also be configured to control a speed of at least one variable speed compressor that delivers refrigerant to a plurality of cryogenic refrigerators based on a pressure differential between a supply line (e.g., supply pressure) and a return line (e.g., return pressure). The controller is also configured to detect a fault in the cryogenic refrigerant system. In response to detecting the fault, the controller initiates fault recovery procedures.

Another example embodiment of a cryogenic refrigerant system may include at least one compressor, where the at least one compressor includes any combination of variable and fixed speed compressors. The system also includes a controller, which is configured to monitor a pressure differential between a supply line and a return line. If the pressure differential is at a value that considered to be greater than a setpoint value (e.g., a state where an excess amount of refrigerant is being supplied), the controller adjusts the operating states of the at least one compressor.

In one scenario, the at least one compressor includes one variable speed compressor and one fixed speed compressor and there is excess refrigerant supply resulting in a higher than normal pressure differential and a pressure differential greater than a system threshold. In order to adjust the system such that the pressure differential is at a value considered to be at a normal operating condition, (e.g., lower the pressure differential to lower than the threshold value), the controller may turn off the fixed speed compressor and adjust the speed of the variable speed compressor to a speed that maintains an adequate supply of refrigerant to cryogenic refrigerators. In another scenario where the variable speed compressor may be running at a minimum speed, the controller is configured to increase the speed of the variable speed compressor to a maximum speed and then turn off the fixed speed compressor.

The threshold value of the pressure differential may be based on a configuration of elements of the refrigerant system. A controller may be configured to pre-store the threshold value. Alternatively, the controller may determine the threshold value based on discovering the configuration of elements of the refrigerant system via discovery communication messages.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIGS. 5A-D are graphs illustrating typical refrigerant (Helium (He)) flows versus requested He flows when switching between one and two motor operation;

DETAILED DESCRIPTION

A description of example embodiments follows.

The teachings of all patents, published applications and references cited herein are incorporated by reference in their entirety.

Prior to discussing helium management control, a discussion of cryopump operation may prove beneficial.

Vacuum pumps such as cryopumps are used to drive a vacuum process chamber to near zero pressure. Near zero pressure, on the order of $10^{-6}$ to $10^{-9}$ torr or even lower, is achieved by removing substantially all the molecules from the vacuum process chamber. The molecules are removed from the vacuum process chamber via the cryogenic refrigerator in the cryopump. A portion of the cryogenic refrigerator is cooled to near absolute zero, typically 10K-20K, causing substantially all of the molecules in the process chamber to condense on the cryogenic array which is cooled by the cryogenic refrigerator. The cryogenic array is typically a set of louvers and baffles to provide a surface area in a compact volume. The condensed gases are therefore reduced to a solid with a low vapor pressure so that a near vacuum is created. Further, the cryogenic array may include an adsorbent substance, such as charcoal, to adsorb molecules which do not condense, such as hydrogen, helium, and neon. The cryogenic refrigerator is powered by a refrigerant working fluid such as helium gas, for example, capable of achieving the temperatures approaching absolute zero.

Cryopumps consume varying amounts of helium depending upon their current operation. A series of cryopumps are connected to a common compressor bank of one or more compressors to maximize the available helium supply. Helium consumption by the cryopumps is monitored and regulated by a controller. By monitoring various operating parameters of each of the cryopumps, an appropriate supply of helium is supplied to each cryopump. Excess helium is redirected to benefit cryopumps which can utilize it. Sparse helium is rationed so as to maintain operation and minimize detrimental effects.

In the refrigerator of a typical cryopump, the working fluid is compressed; the heat of compression is removed by air-cooled heat exchangers; the fluid is further cooled in a regenerative heat exchange matrix; and the gas is then expanded to produce cooling below the ambient temperature. A cryopump must operate effectively at less than 20K to remove gas molecules from the vacuum process chamber. Achieving this low temperature requires the use of highly efficient heat exchangers and a working fluid such as helium gas that remains gaseous at temperatures approaching absolute zero.

Figure 1A:
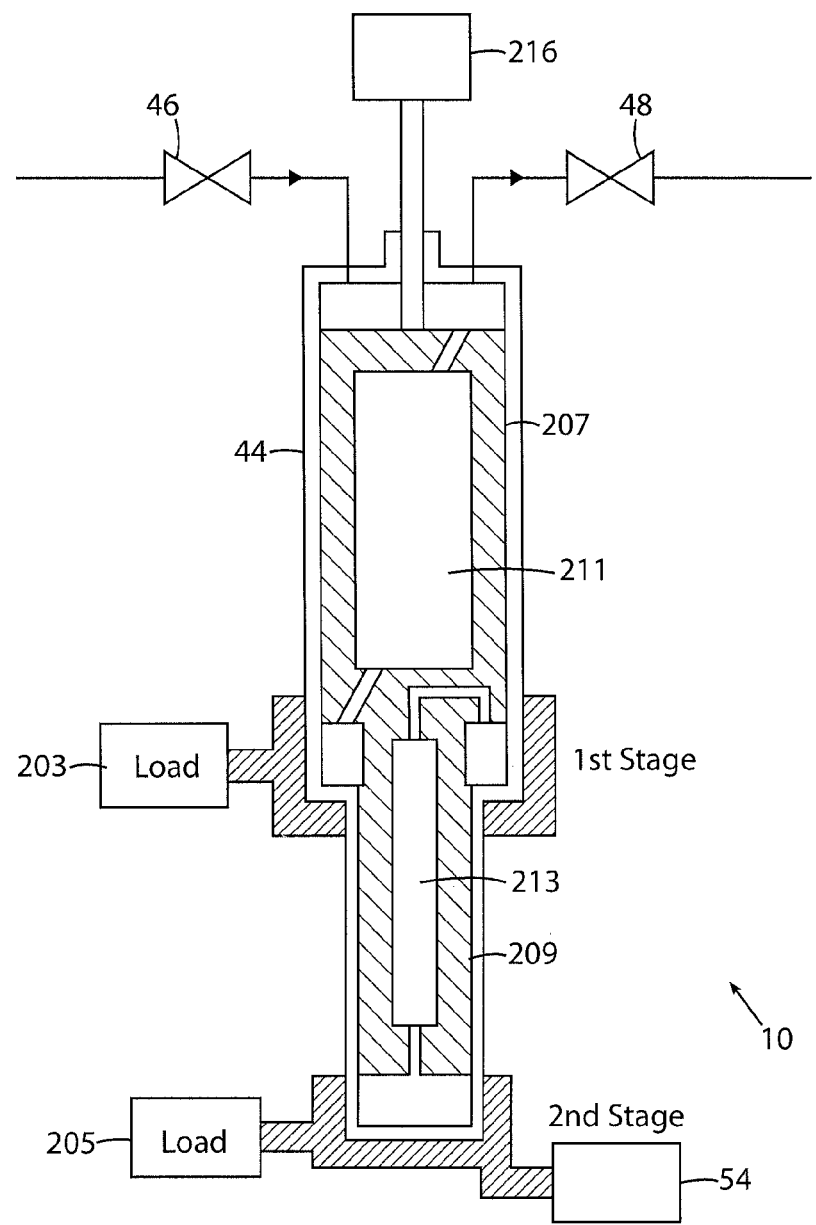
FIG. 1A is a schematic illustration of a typical prior art cryogenic refrigerator

FIG. 1A shows a diagram of the cryogenic refrigerator 10 internals. In the device of FIG. 1a, helium enters the cold finger of the refrigerator through a high pressure valve 46 and exits through a low pressure valve 48. A displacer drive motor 216 drives displacers 207 and 209 in the first stage and second stage cryogenic refrigerators, respectively. The first stage displacer 207 includes a first regenerator 211, and the second stage displacer 209 includes a second regenerator 213. Heat is extracted from first-stage thermal load 203, such as a cryopump radiation shield and frontal array, and second-stage load 205, such as a 10K-20K cryopanel.

The flow of compressed gas refrigerant in the cryogenic refrigerator of a cryopump is cyclic. In the most basic form of a cryogenic refrigerator shown in FIG. 1A, a source of compressed gas, i.e., a compressor, is connected to a first end of a cylinder 44 through an inlet valve 46. An exhaust valve 48 in an exhaust line leads from the first end to the low-pressure inlet of the compressor. With a displacer 207 including a regenerator 211 positioned at a second, cold end of the cylinder, and with the exhaust valve closed and the inlet valve open, the cylinder fills with compressed gas. With the inlet valve still open, the displacer moves to the first end to force the compressed gas through the regenerator to the second end, the gas being cooled as it passes through the regenerator. When the inlet valve is closed and the exhaust valve is opened, the gas expands into the low-pressure discharge line and cools further. The resulting temperature gradient across the cylinder wall at the second end causes heat to flow from the load into the gas within the cylinder. With the exhaust valve opened and the inlet valve closed, the displacer is then moved to the second end, displacing gas back through the regenerator which returns heat to the cold gas, thus cooling the regenerator, and the cycle is completed. In a typical cryopump, the cylinder is called a cold finger and it may have a first stage and a second stage.

To produce the low temperatures required for cryopump uses, the incoming gas must be cooled before expansion. The regenerator extracts heat from the incoming gas, stores it, and then releases it to the exhaust stream. A regenerator is a reversing-flow heat exchanger through which the helium passes alternately in either direction. The regenerator comprises a material of high surface area, high specific heat, and low thermal conductivity. Thus, the regenerator will accept heat from the helium if the temperature of the helium is higher. If the temperature of the helium is lower, the regenerator will release heat to the helium. Alternatively, the cold finger may have only a single stage or more than two stages.

Figure 1B:
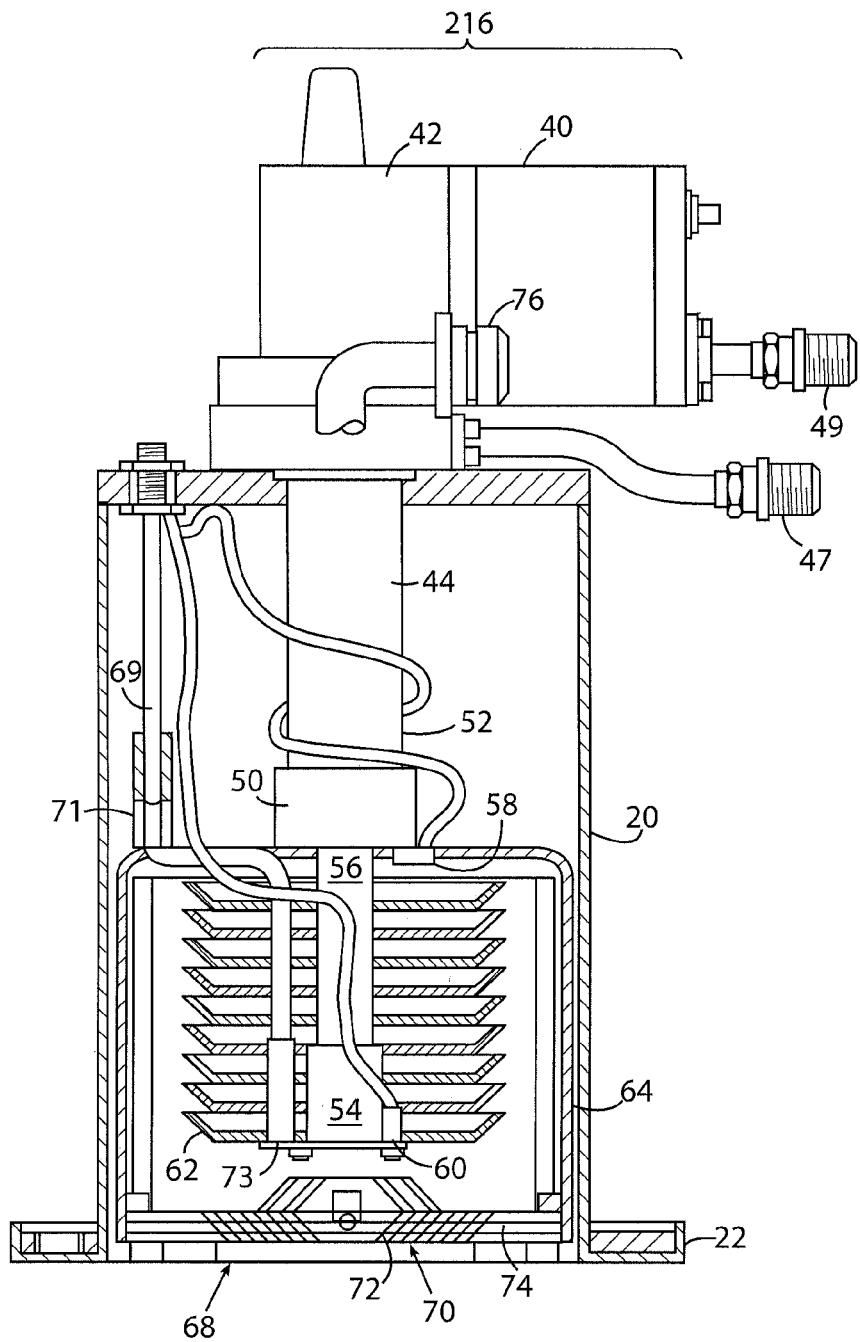
FIG. 1B shows a cutaway view of a typical prior art cryopump including the cryogenic refrigerator of FIG. 1.

FIG. 1B shows a cutaway view of a cryopump including a cryogenic refrigerator. As illustrated in FIG. 1b, much of the cryopump is conventional. In FIG. 1B, a cryopump housing is removed to expose a displacer drive 40 and a crosshead assembly 42. The crosshead converts the rotary motion of the motor 40 to reciprocating motion to drive a displacer within the two-stage cold finger 44. With each cycle, helium gas introduced into the cold finger under pressure through line 47 is expanded and thus cooled to maintain the cold finger at cryogenic temperatures. Helium then warmed by a heat exchange matrix in the displacer is exhausted through line 49.

A first-stage heat station 50 is mounted at the cold end of the first stage 52 of the refrigerator. Similarly, heat station 54 is mounted to the cold end of the second stage 56. Suitable temperature sensor elements 58 and 60 are mounted to the rear of the heat stations 50 and 54.

The primary pumping surface is a cryogenic array 62 mounted to the heat sink 54. This array comprises a plurality of disks as disclosed in U.S. Pat. No. 4,555,907, incorporated by reference in its entirety. Low temperature adsorbent is mounted to protected surfaces of the array 62 to adsorb noncondensible gases.

A cup-shaped radiation shield 64 is mounted to the first stage heat station 50. The second stage of the cold finger extends through an opening in that radiation shield. This radiation shield 64 surrounds the primary cryopanel array to the rear and sides to minimize heating of the primary cryopanel array by radiation. The temperature of the radiation shield may range from as low as 40K at the heat sink 50 to as high as 130K adjacent to the opening 68 to an evacuated chamber. A frontal cryopanel array 70 serves as both a radiation shield for the primary cryopanel array and as a cryopumping surface for higher boiling temperature gases such as water vapor. This panel comprises a circular array of concentric louvers and chevrons 72 joined by a spoke-like plate 74. The configuration of this cryopanel 70 need not be confined to circular, concentric components; but it should be so arranged as to act as a radiant heat shield and a higher temperature cryopumping panel while providing a path for lower boiling temperature gases to the primary cryopanel.

Although cryopumps have been described with the use of drive motors and reciprocating displacers, alternative refrigeration systems such as pneumatic or pulse tube refrigerators may be employed.

Figure 2:
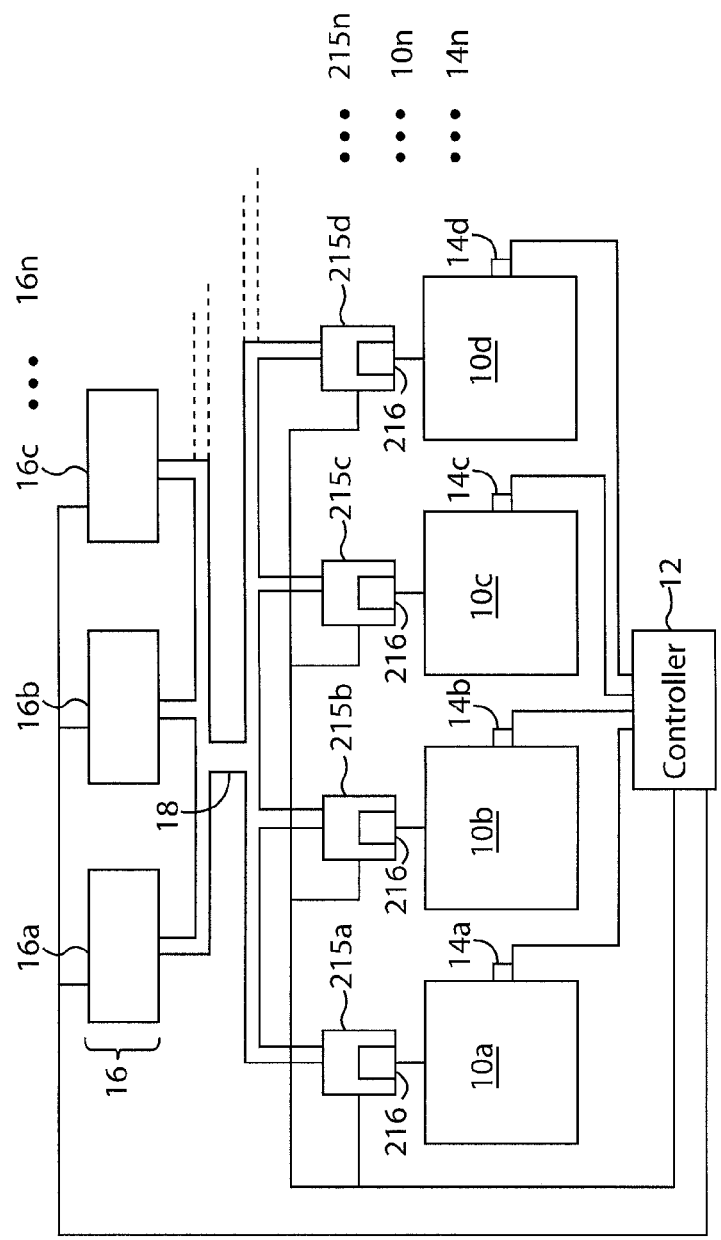
FIG. 2 shows a block diagram of a cryogenic refrigeration system master controller connected to a plurality of cryopumps and compressors.

FIG. 2 shows a bank of compressors used to supply refrigerant to a series of refrigerators in cryopumps. Referring to FIG. 2, the common compressor bank 16 includes compressors 16a-16n which supply helium refrigerant to a manifold 18. The manifold 18 is connected to a series of cryopumps 10a-10n in conjunction with the refrigerator controllers 215a-215n. The slave controllers each control a displacer drive 216 which drives a displacer which reciprocates in the cold finger as the refrigerant gas expands. The displacer drive 216 is used to regulate the cooling rate of the pump depending on the quantity of refrigerant supplied. A cryogenic refrigeration system controller 12 (controller) is connected to each of the refrigerator controllers 215a-215n controlling the displacer drive 216 and is used to increase or decrease the quantity of refrigerant supplied to the refrigerator/cryopumps 10. The controller 12 may be a hardware circuitry configured to communicate with individual compressors and cryo-devices and may be further configured to manage group refrigeration system activities such as group regeneration and helium management. Alternatively, controller 12 may be employed as logic that may exist within any element of the refrigeration system such as within a cryopump or compressor. Each of the refrigerators/cryopumps 10 has one or more sensors 14a-14n which provide feedback to the controller 12. The controller 12 therefore regulates all the cryopumps 10 connected to it by receiving signals from the sensors 14 and computing a helium quantity demand for each pump 10 based on the signals sent from the sensors 14 and from the total helium available from the manifold, as will be described in more detail below. Alternatively, demand may be calculated by the cryopumps 10 and the demand may be sent to controller 12. In addition, the controller 12 is connected to each of the compressors 16a-16n in the compressor bank 16. The system controller 12 receives supply pressure and return pressure feedback from each of the compressors 16a-16n and using that information, the controller 12 controls the status (e.g., off or off) and the speed at which each of the compressors 16a-16n outputs helium.

It should be noted that a refrigeration control system is described in conjunction with an example cryogenic refrigerator in a cryopump. The refrigeration control system may be used in conjunction with a refrigerant supply for a variety of cryogenic refrigerators including single and multiple stage devices. A cryopump as described herein may, for example, be a water pump, cooled by a single stage cryogenic refrigerator, such as that disclosed in U.S. Pat. No. 5,887,438, entitled "Low Profile In Line Cryogenic Water Pump," incorporated by reference in its entirety, and assigned to the assignee of the present application, or other helium driven cryogenic device. Alternatively, cryogenic refrigerators such as Stirling, Gifford-McMahon, and pulse tube may be employed.

Depending on the cooling operation state and cooling demand on the refrigerator of the cryopump, varying refrigerant consumption rates occur. A cool down operation brings the temperature of the cryopump from an ambient state down to the cryogenic temperatures, and requires the most refrigerant for the refrigerator. Once cryogenic operating temperatures have been achieved, a normal operating mode maintains the temperature and requires a generally stable flow of helium. A regeneration operation warms up the cryopump to release accumulated, condensed gas and requires little or no refrigerant during warming and while the cryopump is warm. Other factors can affect the refrigerant consumption rate. During cool down, the cryopump gradually consumes more helium as it becomes colder, approaching normal operating temperatures. At normal operating temperatures, vacuum process activities occurring in an attached vacuum process chamber may generate heat, increasing the heat load and refrigeration required to maintain appropriate operating temperatures.

The aggregate refrigerant consumption rate of all the refrigerators in the cryopumps connected to the common refrigerant supply can be used to determine an aggregate refrigerant demand. Similarly, the refrigerant availability of the compressor or compressors contributing to the common refrigerant supply can be used to determine a refrigerant availability of the system. As indicated above, the actual consumption rate of each cryopump varies depending on a variety of factors. At a particular point in time, the refrigerant availability of the system may exceed the aggregate refrigerant demand, indicating excess refrigerant in the system. Similarly, if many cryopumps are experiencing a period of high refrigerant consumption, the aggregate refrigeration demand may exceed the refrigerant available, indicating refrigerant sparsity.

With increased demand for higher efficiencies, the efficient control of a variable speed compressor operation is helpful. For cryogenic vacuum systems, the optimum solutions is to provide the cryogenic refrigerators with only the amount of refrigerant (helium) needed for the refrigerator to maintain first and second stage temperatures. One solution is to have the compressor vary its speed in order to deliver only the mass flow of refrigerant that is being consumed by refrigerators. Such operation results in significant savings in operating cost of the compressors.

Figure 3:
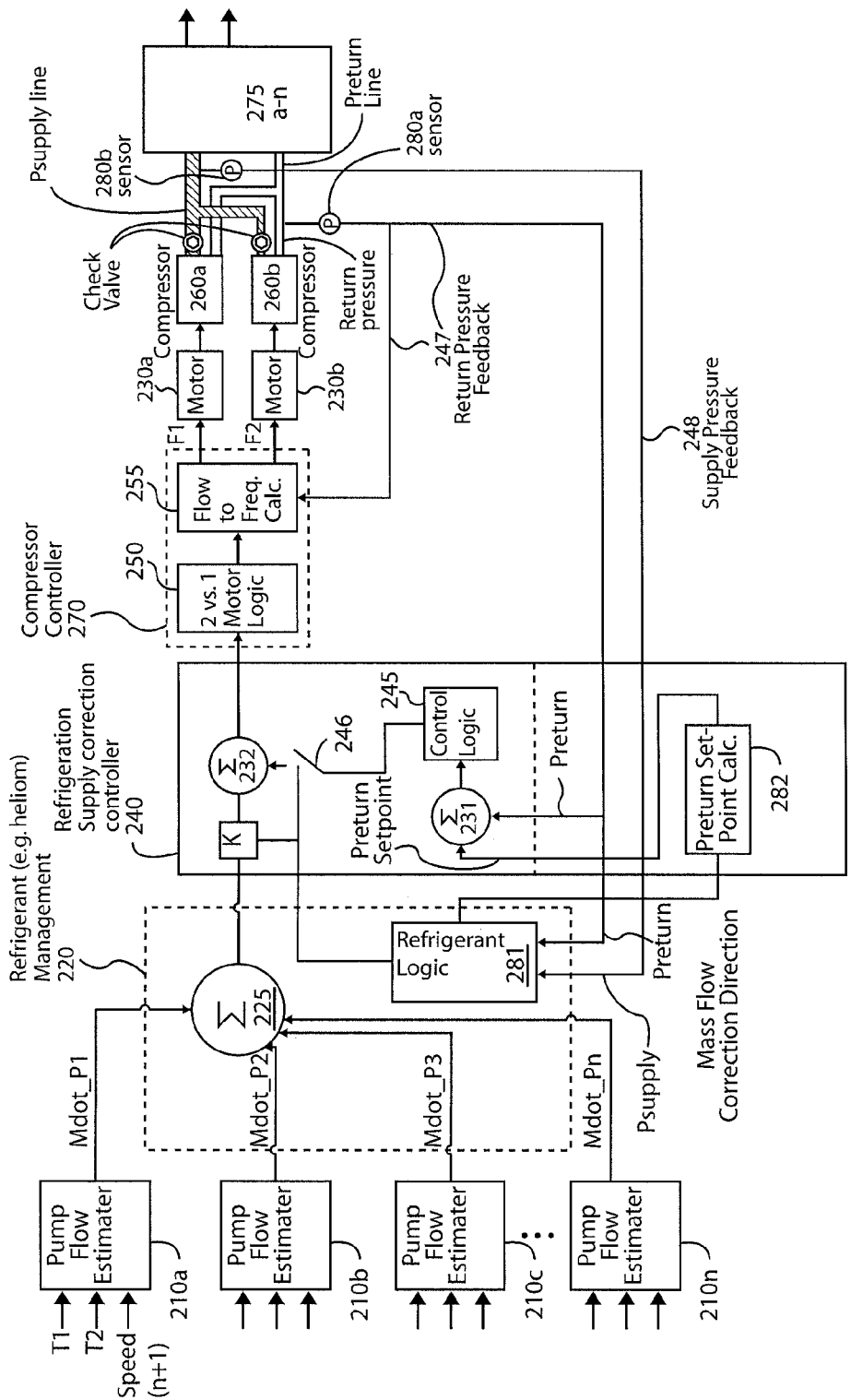
FIG. 3 shows a block diagram of a refrigeration system for controlling supply of a refrigerant.

FIG. 3 is a block diagram of a refrigeration system for controlling supply of a refrigerant to refrigerators in cryopumps. A plurality of refrigerators 275 requiring a refrigerant are coupled to compressors 260a-b and cryopump refrigerator flow demand estimators 210a-n. Each cryopump flow estimator 210a-n receives metrics from a refrigerator 275a-n that are used to estimate an amount of refrigerant that the refrigerators 275a-n demand. The cryopump refrigerator flow demand estimators 210a-n may receive the metrics from the refrigerators via direct wired communications or wireless communications. While FIG. 3 depicts a cryopump system, in alternative embodiments cryopumps may be replaced by single or multi-staged refrigerators.

Alternatively, the cryopump refrigerator flow demand estimators 210a-n may be processors hardwired to the refrigerators 275 a-n to monitor the refrigerators. Although plural cryopump refrigerator flow demand estimators 210a-n are depicted, it should be noted that the plurality of refrigerators 275a-n may communicate the metrics to a single pump flow estimator.

The refrigerators 275 a-n may employ sensors that record and track the metrics. The sensors then send the metrics to the cryopump refrigerator flow demand estimators 210a-n. The metrics received by the cryopump refrigerator flow demand estimators 210a-n may include Psupply, Preturn, T1 and T2, refrigerator cycling speed, refrigerator specific parameters and potentially other operating parameters associated with each refrigerator 275 a-n. The cryopump refrigerator flow demand estimators 210a-n use the metrics to calculate an estimated refrigerant demand for each refrigerator individually or in an aggregated basis.

A refrigerant management system 220 is coupled to the pump flow estimators 210a-n and receives communications that include the estimated refrigerant demand from each of the cryopump refrigerator flow demand estimators 210a-n. At 225, the refrigerant manager 220 then calculates a total aggregate demand (mass flow request) for the refrigerant based on the communications from the cryopump refrigerator flow estimators 210a-n.

The calculated total aggregate demand for refrigerant is an estimate that has error associated with it. For example, the error may range anywhere within 0-20%. Due to such possible error, the refrigerant management system 220 sends the calculated total aggregate demand to a refrigerant supply correction controller 240 to determine an amount of refrigerant to supply to the plurality of refrigerators 275 *a-n*. This determination is made by summing the calculated total aggregated demand and a refrigerant supply correction (mass flow correction). The refrigerant supply correction controller 240 calculates the refrigerant supply correction as described below.

Using refrigerant logic 281, the refrigerant management system 220 determines the state of the refrigeration system. For example, the refrigeration system may be in one of the following states: temperature control, cool down, or off. The state of the refrigeration system may be determined by use of sensors throughout the refrigerant system. The controller may assign a unique numerical value to a message that allows the components of the refrigeration system to know the status of the system including but not limited to faults and operating mode. The refrigerant supply correction controller 240 may adjust the total aggregated demand by a predetermined factor based on the state of the system at 225.

The refrigerant management system 220 also receives return pressure (Preturn) and supply pressure (Psupply) metrics from low pressure return lines and high pressure supply lines via feedback loops from the compressors 260*a-b* to determine which direction to correct return pressure setpoint. The refrigerant management system 220 receives the Preturn and Psupply metrics from sensors 280*a* and 280*b*, respectively, that monitor the return pressure and supply pressures. The sensors 280*a* and 280*b* are coupled to Preturn line and Psupply line, respectively.

The return pressure setpoint calculator 282 calculates the return pressure setpoint by using information from refrigerant logic 281 related to the state of the refrigeration system and whether a current supply of refrigerant should be increased or decreased, as described above. Refrigerant management system 220 using the refrigerant logic 281 determines whether the current supply of refrigerant should be increased or decreased by calculating a differential pressure between the supply pressure and return pressure of the compressors. The differential pressure is simply the difference between the supply pressure and the return pressure. The refrigerant management system 220 receives Psupply and Preturn metrics via feedback loops 247 and 248. The refrigerant logic 281 may calculate an average differential between the supply pressure and return pressure over a period of time. For example, the refrigerant logic may obtain the average differential over a period of two minutes.

Generally for some cryogenic refrigeration systems, a normal or static condition occurs when the supply pressure is 400 PSI and the return pressure is 200. Under such conditions, the refrigerant management system 220 determines that the supply of refrigerant should remain unchanged or static and neither increase nor decrease.

However, where the differential pressure is determined to be less than a lower differential pressure threshold, for example at 190 psi (i.e., the normal differential pressure minus a configurable offset), the refrigerant management system 220 determines that a large reduction in the differential pressure has occurred and is outside of the desired operating range. Such a large reduction indicates to the refrigerant management system 220 that the refrigerators 275 *a-n* are receiving an inadequate supply of refrigerant and the supply of refrigerant should be increased. Conversely, where the differential pressure is determined to be greater than an upper differential pressure threshold, for example at 210 psi, (the normal differential pressure plus a configurable offset), the refrigerant management system determines that the differential pressure has increased outside the desired operating range. Such an increase in differential pressure indicates to the refrigerant management system 220 that the compressors are delivering too much refrigerant and wasting refrigerant through a bypass valve (not shown) and the supply of refrigerant should be decreased. Typical system operation (with cryopumps in temperature control) maintains operation within the upper and lower differential pressure thresholds. However, in cases where loads are changing rapidly, mass flow demand estimates may have significant error, or a fault may have resulted such as a loss or gain of a compressor or cryopump, this correction mechanism will adapt over a period of minutes until the compressor delivers the flow required by the pumps.

Once the refrigerant management system 220 determines whether the supply of refrigerant should remain static, increase, or decrease, the refrigerant management system 220 using refrigerant logic 281 determines whether to increment or decrement a return pressure setpoint. The return pressure setpoint calculator 282 receives a message from the refrigerant logic indicating whether the return pressure setpoint needs to be incremented or decremented. Upon receiving this message, the return pressure setpoint calculator 282 adjusts a return pressure setpoint to control the return pressure in the low pressure return line.

The return pressure is controlled rather than supply pressure due to the fact that return pressure fluctuations generally dominate the cause of the collapse or increase in the differential pressure between the supply pressure and return pressure. This is due to the fact that supply pressure fluctuations are generally nominal and thus have minimal impact on the differential pressure while return pressure fluctuations are substantive. In alternative embodiments, supply pressure may be monitored and controlled rather than return pressure.

The refrigeration supply correction controller 240 calculates the return pressure (Preturn) setpoint by increasing or decreasing the setpoint by an incremental value via Preturn setpoint calculator 282. The Preturn setpoint may be initialized at the transition to a new state, then updated through increments in the refrigeration supply correction controller. Once the return pressure setpoint is calculated the refrigerant supply correction controller 240 calculates a return pressure error by calculating a difference between the return pressure setpoint and the return pressure at 231. The refrigerant supply correction controller 240 receives the return pressure metric via a return pressure feedback loop 247. The refrigerant correction controller 240 then calculates the refrigerant supply correction using refrigerant correction control logic 245 and refrigerant aggregated demand from refrigerant management system 220. The refrigerant supply correction may be calculated as the output of the control law with the return pressure error as an input (i.e., the convolution sum of the return pressure error signal with a control law difference equation.) In this case, a proportional control logic is employed by the control logic 245, where the refrigerant supply correction is calculated using the following formula: return pressure proportional constant*return pressure error. The refrigerant supply correction controller 240 then determines the amount of refrigerant to supply to the refrigerators based on the total aggregated demand from refrigerant management system 220 and the calculated refrigerant supply correction, specifically the sum of those signals at 232.

Also, if the system state is in cool down, the correction loop may be disabled, as illustrated by open switch 246.

The refrigerant supply correction controller 240 notifies a compressor controller 270 of the amount of refrigerant to supply to the refrigerators 275. Based on this notification, compressor motor logic 250 determines an operational state of the plurality of compressors 260*a-b*. The compressor controller 270 may control the operational state of multiple pumps coupled to a single compressor or multiple separate compressors. The operational state of the compressors determines a number of compressors to be on and off. In an example embodiment, the plurality of compressors 260*a-b* comprises only two compressors. In such an embodiment, the motor logic 250 determines whether both compressors should be operating or if only one compressor should be operating.

The compressors 260*a-b* are coupled to compressor pump motors 230*a-b* that drive the compressors 260*a-b*. The motors 230*a-b* may operate and drive the compressors 260*a-b* via a rotary pump, piston pump, scroll pump or any other appropriate driving means.

The compressors 260*a-b* may be variable speed compressors and are able to supply refrigerant to the refrigerators at varied speeds by adjusting speeds at which the motors 230*a-b* run. A flow to frequency calculator 255 determines the speed of the compressor motors 230*a-b* for the compressors 260*a-b* that are determined to be on. The speed of the compressor motors 230*a-b* may be determined as a function of the calculated amount of refrigerant to supply to the refrigerators and the return pressure. Specifically, frequency=mass flow/(K*return pressure).

The description above segregates functions into items described as controllers. These functions may be grouped into a single or any combination of controllers as well as be located separately or on one or more components of the cryopump/cryogenic refrigerator system.

Alternatively, if the amount of refrigerant to supply to the refrigerators exceeds the capacity of all the compressors running at maximum capacity, the refrigerant management controller 220 may adjust the speed of at least one refrigerator of the plurality of refrigerators.

Unlike previous approaches, the current refrigerant supply control loop does not rely on differential pressure for a primary feedback mechanism. Rather, the method utilizes feedforward flow control (aggregated demand for refrigerant) assisted by return pressure control. Differential pressure is merely used to provide adaptive adjustments to refrigerant supply when the differential drifts outside of a desired operating range. Such causes for this drift may be attributed to poor estimated demand for refrigerant or supply by the compressor or to a loss or gain of refrigerators or compressors in the refrigeration system or to significant load variations resulting in rapid refrigerant demand changes.

As stated above, higher efficiencies of supplying refrigerant may be obtained by the use of variable speed compressors. Higher efficiency levels may be obtained by adding the ability to supply refrigerant from either a single compressor or two compressors based on the calculated amount of refrigerant to supply to the refrigerators. Transitioning from an operational status of two variable speed compressors to an operational status of a single variable speed compressor or vice versa must be done without significantly impacting the differential between the supply pressure and return pressure. In addition, switching between operational statuses must also be done in a manner to maintain a high level of reliability from the compressors.

Figure 4:
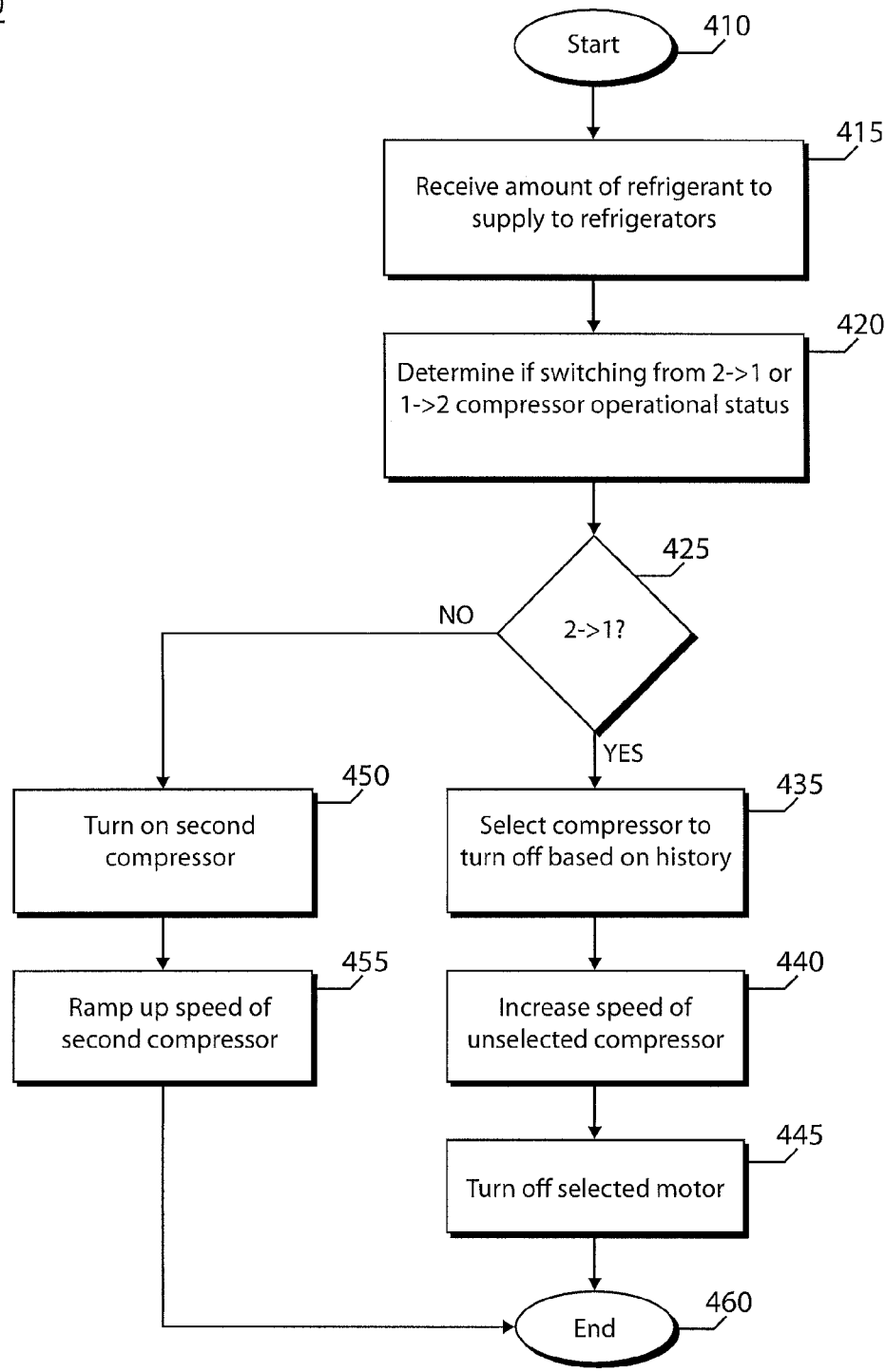
FIG. 4 shows a flow diagram of a method for determining a number of variable speed compressors to operate.

FIG. 4 shows a flow diagram of a method 400 for determining a number of variable speed compressors to operate. Referring to FIG. 3, the method 400 is carried out in motor logic 250. Prior to beginning the method, a determination is made as to the maximum capacity of both variable speed compressors running simultaneously. At step 410, the method 400 begins. At step 415, a compressor controller 270 receives a command to supply an amount of refrigerant.

At step 420, using the compressor motor logic 250, it is determined whether to operate with a single variable speed compressor running or with both variable speed compressors running. This determination is made by determining a transitional threshold which is computed by determining whether the command to supply an amount of refrigerant is greater than or less than a maximum capacity of a single variable speed compressor. The maximum capacity of the single variable speed compressor may be calculated as half the maximum capacity of both variable speed compressors operating simultaneously. It should be noted this value is an estimate and the maximum capacity of a single variable speed compressor is slightly more than half the maximum capacity of both compressors running due to the fact that running two compressors simultaneously reduces the DC bus voltage.

At step 425, motor logic 250 determines that the refrigeration system should transition to a single variable speed compressor operational state from a double variable speed compressor operational state. In other words, it is determined that one of the two variable speed compressors should be turned off. As stated above, this determination is made if the command to supply an amount of refrigerant is less than the maximum (threshold) capacity of a single variable speed compressor. To account for uncertainties in transitioning due to noise level in flow estimates, the determination may be made if the amount of refrigerant needed to be supplied is less than the maximum capacity of a single variable speed compressor less a predetermined hysteresis value. For example, the hysteresis value may be 10 standard cubic feet per minute (SCFM). In addition to using a hysteresis value to account for uncertainties, it may be required that the demand be less than maximum capacity less the hysteresis value for a predetermined period of time or debounce period. Hysteresis is used to eliminate frequent on/off cycling of the motors which would have an adverse effect on compressor reliability. It should be noted that debounce delay is only applied when turning a motor off, when turning a motor on, very little delay is applied.

At step 435, upon a determination to switch from a two compressor operational state to a single compressor operational state, the motor logic 250 selects which of the two compressors to turn off. This selection may be based on a history of turn offs of each motor. For example, the motor logic 250 may alternate between the two compressors with each determination to switch to a single compressor operational state, alternate between motors for a period of time, or alternate between motors in using any other pattern. The method for cycling between compressors to turn on and off ensures that power cycling is shared equally between the two compressors thereby maintaining a high degree of reliability while cycling the compressors on and off.

At step 440, prior to turning the selected compressor off, the speed of the unselected motor is increased or ramped up to a speed equal to or greater than the speed required to supply the needed refrigerant. The increase in speed is necessary to ensure adequate supply of refrigerant. At step 445, the selected compressor is turned off.

At step 420 and 425, if it is determined that the refrigeration system should transition to a double variable speed compressor operational state from a single variable speed compressor operational state, then the second compressor is turned on. As stated above, this determination is made if the command to supply an amount of refrigerant is greater than the maximum (threshold) capacity of a single variable speed compressor. To account for uncertainties in transitioning, the determination may be made if the amount of refrigerant is greater than the maximum capacity of a single variable speed compressor. Additionally, the determination to switch from a single compressor state to a double compressor state may be made only if the amount of refrigerant exceeds the threshold value for a very short predetermined period of time to ensure adequate supply of refrigerant to the refrigerators.

At step 450, upon a determination to switch to a single compressor operational, the compressor controller 270 turns on the second variable speed compressor. At step 455, the method 400 ramps up the speed of the turned on compressor and allows the turned on motor to settle. At step 460, the method 400 ends.

Advantageously, the method 400 allows compressors to run from a single compressor running at minimum speed to two or more compressors running at full speed; for example 35 Hz for a single compressor to two compressors running at 70 Hz. This allows a greater versatility and range for supplying refrigerants to refrigerators. The method 400 may also be used for any combination of fixed and variable speed compressors. In addition, at least one fixed speed compressor may be turned off when the refrigerant demand is supplied by at least one variable speed compressor.

Alternatively, this same method of operation may be applied to more than one compressor pump in a single compressor structure. One compressor pump within the structure could remain operational when demand is low instead of running all of the compressor pumps. The ability to turn off one or compressor pumps while having one or more others within the structure continue operating to meet helium demand during periods of low demand provides significant improvements in energy efficiency.

Figure 5A:
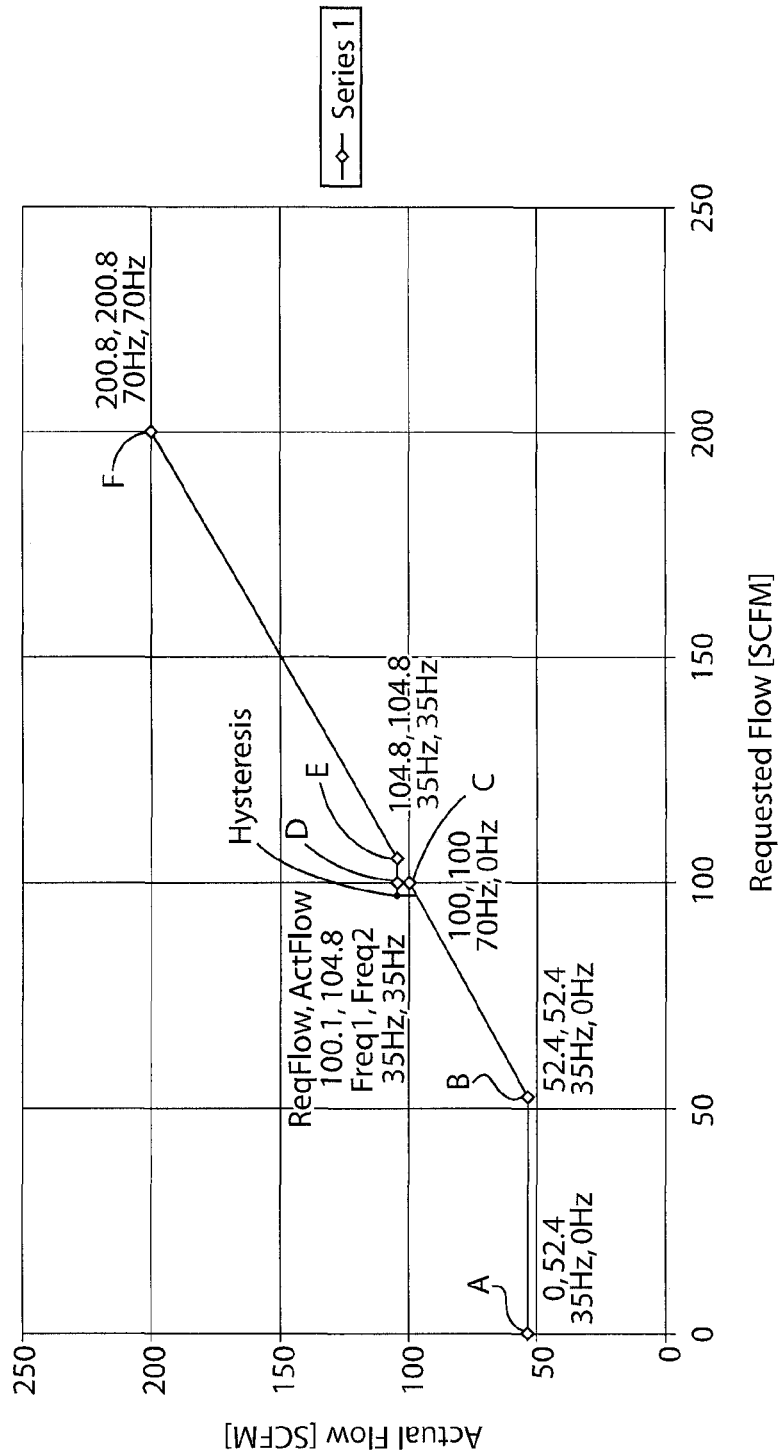
Figure 5B:
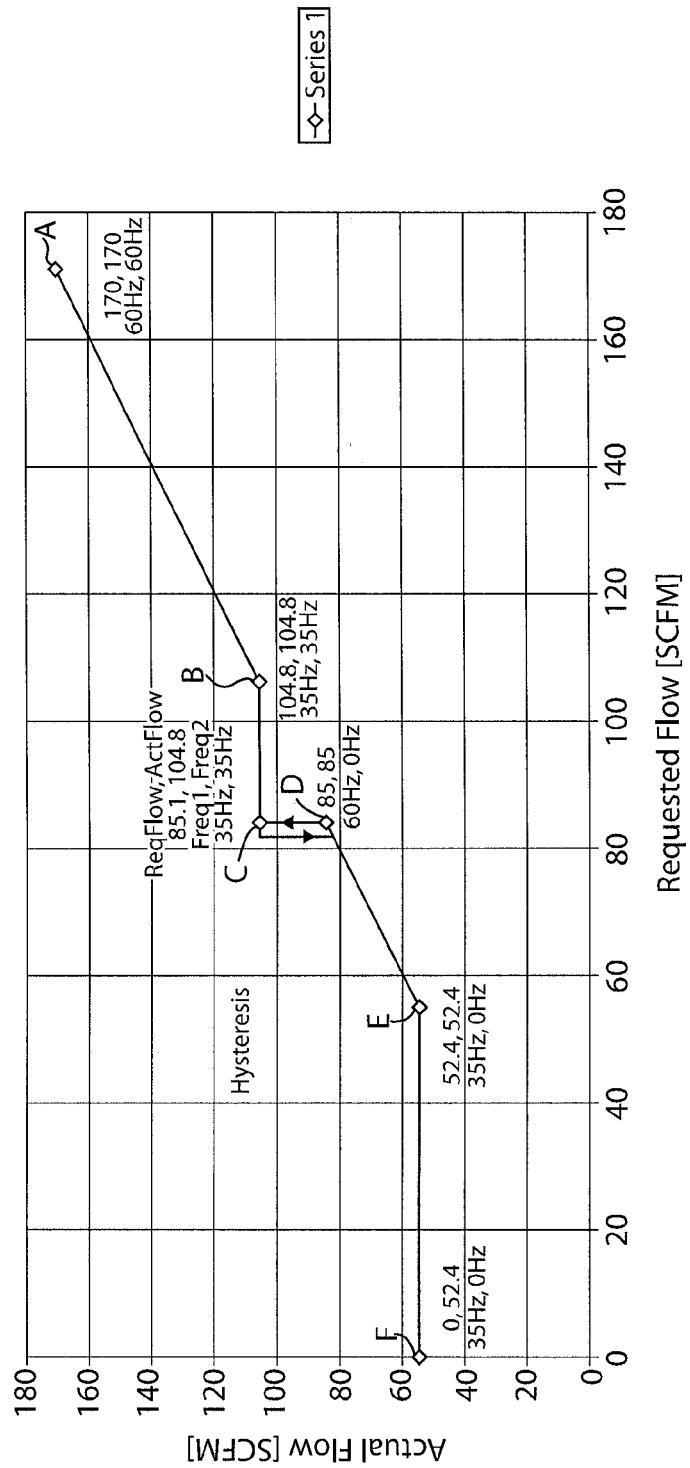
Figure 5C:
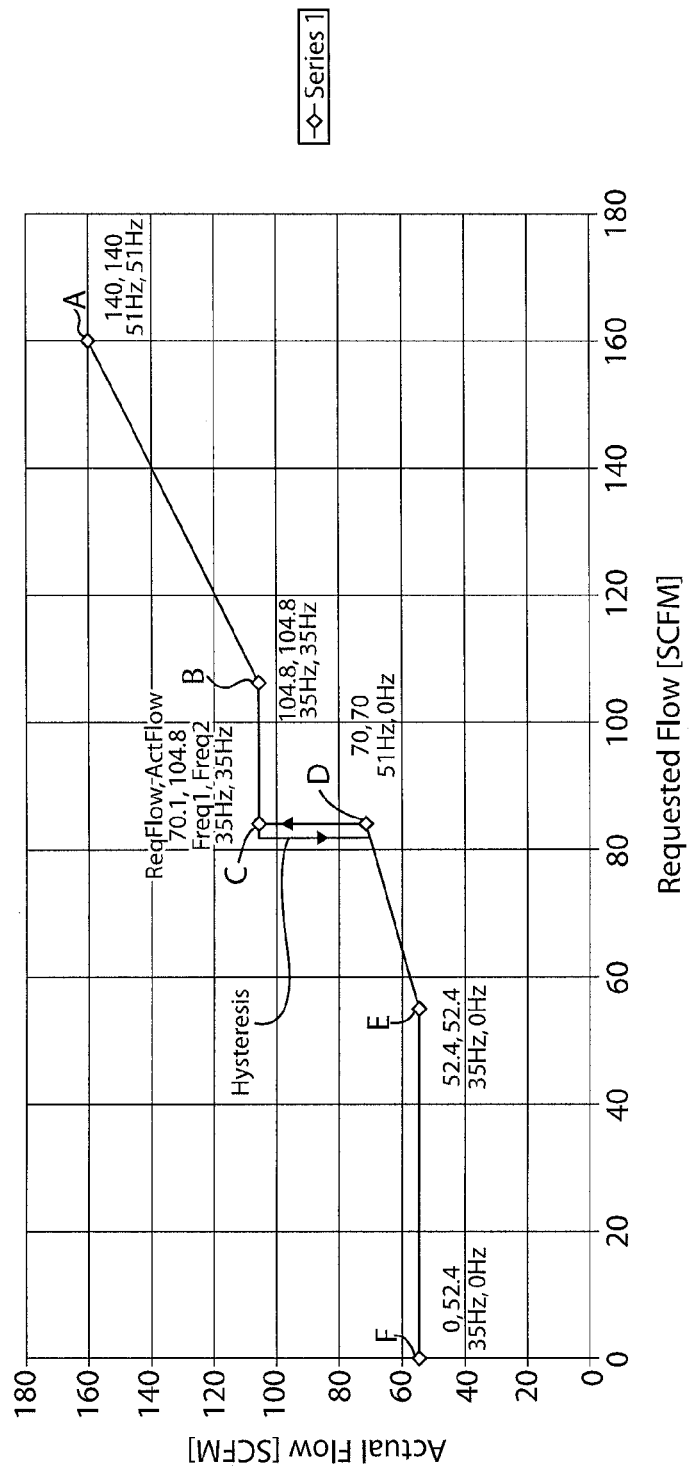

FIGS. 5A-D are graphs illustrating typical refrigerant flows versus requested flows when switching between one and two compressor or compressor pump operation as described above in reference to FIG. 4. FIG. 5A illustrates a graph for a high voltage or low voltage with an extended operating frequency range scenario. FIGS. 5B-C illustrate graphs for a low voltage (no extended range) scenario. In these examples, there is an interruption of the linear function of requested versus actual flow at the point where the second motor is turned on/off. The interruption for the linear function in FIG. 5A-5C is due to the fact that a full capacity of a single compressor may be less than the minimum capacity of two compressors. The interruption in the linear function is smaller in FIG. 5A than in FIGS. 5B-C due to the different power supply and compressor motor drive circuits that result in a greater maximum operating speed of the a single compressor in FIG. 5A. FIG. 5D is a table illustrating the state of a refrigeration system at each reference point of FIG. 5C.

As stated above, FIG. 5A illustrates a graph for a high voltage scenario. The graph plots actual flow on the y-axis versus requested flow on the x-axis. In addition, at each point of the graph, the speed or frequency of each of the two variable speed compressors is shown. Points A and B illustrate a state of the refrigeration system where only one of the two variable speed compressors is turned on and operating. This is illustrated by showing that a second frequency is 0. Point C illustrates a point where a transition needs to be made to a two variable speed compressor state. As shown moving from one to two compressors a hysteresis of 4.8 SCFM ensured that the transition only occurs when a requested flow is greater than 100 SCFM. Conversely, at point D, a decision may be made to move from a two compressor state to a single compressor state. Here, hysteresis ensures that the transition only occurs if the requested flow is less than 100 SCFM. Points E and F illustrate a scenario where the compressors are running in a two compressor state. Point E shows a scenario where the two compressors are both running at minimum capacity while Point F shows a scenario where the two compressors are both running at maximum capacity.

FIG. 5B illustrates a graph for a low voltage (no extended frequency range) scenario at 208 VAC. The graph plots actual flow on the y-axis versus requested flow on the x-axis. In addition, at select points of the graph, the speed or frequency of each of the two variable speed compressors is shown. FIG. 5B is similar to FIG. 5A, however transition from one to two compressor and two to one compressor states occur at a different requested flow due to the fact that a full capacity of a single compressor is less than the minimum capacity of two compressors and this difference is greater in a low voltage scenario without extended frequency range circuitry.

FIG. 5C is similar to FIG. 5B and illustrates a graph for a low voltage scenario at 180 VAC. The graph plots actual flow on the y-axis versus requested flow on the x-axis. In addition, at selected points of the graph, the speed or frequency of each of the two variable speed motors is shown. Points A-F of the graph illustrates a state of a refrigeration system based on requested flow for refrigerant and actual flow. In addition, the graph illustrates the state of each compressor in the system. Table 5D references each point, A-F, of FIG. 5C and shows the value for requested flow, actual flow, and frequency of each compressor.

Figure 6:
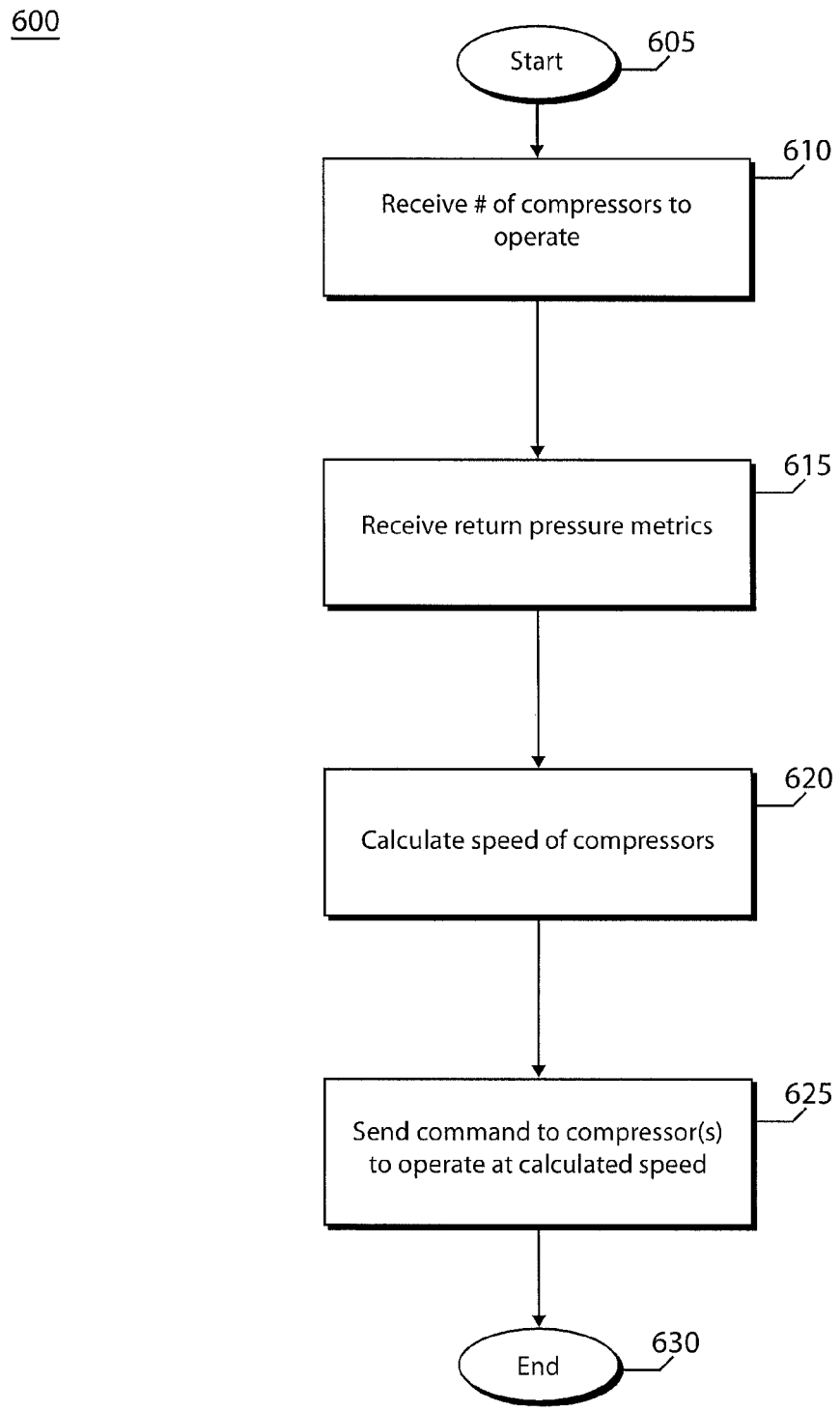
FIG. 6 shows a flow diagram of a method for determining the speed of operating compressors.

FIG. 6 shows a flow diagram of a method 600 for determining the speed of operating compressors. Referring to FIG. 3, the method 600 is carried out by the flow to frequency calculator 255. At step 605, the method begins. At step 610, the flow to frequency calculator 255 receives a command from the compressor motor logic including information relating to the number of compressors to run and the amount of refrigerant to supply to the refrigerators. In addition, at step 615, the flow to frequency calculator 255 receives return pressure metrics via the return pressure feedback loop.

At step 620, the flow to frequency calculator 255 calculates the speed at which the two compressors should run based on the information received at steps 610 and 615. This calculation employs combines the ideal gas law: PV=nRT and the formula for volume flow rate: V=compressor volumetric efficiency constant (K)*speed of the compressor (frequency (F)). Combining the two equations and solving for frequency yields the equation F=mass flow/(K*return pressure).

However, simply requesting the compressor(s) to run at a frequency, F, may not yield an actual speed of 'F'. This may be due to the type of motor employed by the compressor(s). For example, if the compressor(s) uses a synchronous AC motor, this equation is correct as is, however if an AC induction motor is used, the above equation solving for frequency may need to be compensated for motor slip. Thus, the frequency calculator must command the compressors to run at a higher frequency than that would be calculated above. Motor slip may be estimated using any known method known in the art. At step 625, the flow to frequency calculator 255 sends a drive signal to the compressor pump (s) to drive the motor at the calculated frequency (speed) adjusted based on the type of motor used. At step 630, the method ends.

It should be noted that the compressors may run at same speed or different speeds. Compressor motors run at the same speed to eliminate a problem of beating at difference frequencies, to reduce mechanical vibration and audible noise. If the compressor pumps are in a same frame, operating frequencies may be the same to eliminate beating at different frequencies. However, separate compressors may be run at different speeds. When establishing operating frequencies for separate compressors, selection of frequencies may also depend on operating efficiency characteristics of the individual compressors. Accumulators may also be used to minimize the effect of beating.

In addition, the flow to frequency calculator 225 may be configured to calculate the speed of a multitude of mechanical compression pumps within a single compressor system. For example, rather than determining the speed at which separate compressors run, the flow to frequency calculator 225 may determine the speeds of multiple mechanical pumps within a single compressor system. Alternatively, for a refrigerator system that has a multitude of separate compressors, the flow to frequency calculator 225 may be configured to determine the speeds of the multitude of separate compressors. The multitute of separate compressors may be a plurality of variable speed compressors or a combination of variable speed compressors and fixed speed compressors.

The methods of varying compressor speeds to achieve high energy efficiency for cryogenic vacuum pump systems and cryogenic refrigeration systems described above relies on a combination of refrigerant flow demand and the return pressure of the system to establish the required refrigerant supply of the compressors. Speed and operating states of the compressors and compressor pumps are determined by the corrected aggregated flow demand of the cryogenic refrigerations/cryopumps. Additionally, the return pressure may not need to be corrected in smaller systems.

Alternative methods for varying compressor speeds may include utilizing a total refrigerant requirement defined by refrigerant management logic. The compressor speeds may be varied to exactly meet the uncorrected aggregate demand for refrigerant. This method of control works well when the refrigerant demand requirements of the refrigerators on the system under the range of operating conditions are known accurately. Algorithms may be implemented to utilize this information for compressor speed control.

Controlling refrigerant supply directly based solely on return pressure measurements may be implemented as a means of controlling refrigerant from one or more compressors/compressor pumps. The operating speed or state of the compressors/compressor pumps will be increased or decreased based on the measured return pressure. Further, a lookup table or output algorithms may be used in a control loop. Because refrigerant mass flow is directly related to return gas density (pressure), insufficient flow is indicated by a rise in return pressure and excess flow is indicated by a fall in return pressure. The compressor speed may be controlled to maintain return pressure within a specified range to assure appropriate refrigerant is supplied within a variable refrigerant demand environment.

In another example method, direct measurements of refrigerant flow in a bypass loop with a bypass valve may be made. Excess refrigerant flow in the bypass loop indicates an excess of flow supply to the entire system. If the measurements indicate such an excess, the compressor speeds may be adjusted to maintain a small excess refrigerant flow within the bypass loop.

Additionally, a motor driven bypass valve may be implemented in lieu of a spring force driven valve. Further, by positioning flow regulating member in the valve allows an indirect measurement of refrigerant flow in the bypass loop. The compressor speeds may then be adjusted based on valve position (bypass flow rate) to minimize bypass flow.

In addition, for any of these solutions upon exceeding the return pressure at maximum speed, the refrigerant management logic may reallocate available helium thereby lowering return pressure to an acceptable level.

Versatility of Compressor with Mass Flow Control

A method and corresponding refrigeration system relates to enabling a compressor system with mass flow control to interface with any system utilizing a refrigerant such as Helium. This includes a refrigerant flow control from existing CTI cryogenic systems such as OnBoard® and OnBoard® IS cryopumps and refrigerators as well as the flexibility of controlling one or more compressors and compressors and refrigerators/cryopumps from other manufacturers. Both fixed speed and variable speed compressors may be combined in any combination as long as there is at least one variable compressor present. With multiple compressors combined, fixed speed compressors could be turned on and off depending on demand in addition to varying the speed and operating state of the compressor with variable speed capabilities.

Using return pressure and differential pressure allows a compressor to connect to any refrigerant system and control the mass flow of refrigerant without receiving data from the system. The control algorithm may not respond as quickly as feedforward of refrigerant demand, but is more flexible because there is no need to receive communications from the refrigeration system. With feedforward, refrigerant consumption may be provided directly in units of SCFM or in the form of refrigerator variables which can be used to estimate the refrigerant mass flow consumption. Additionally, feedforward of refrigeration consumption/demand may be used alone or in conjunction with return pressure or differential pressure.

An interface between the compressor and the cryopumps/refrigerators is composed of two parts, the physical interface and the data interface. For flexibility, at least one of the following physical interfaces may be employed: RS-232 serial, Bitbus to accommodate Brooks legacy products, Ethernet and DeviceNet. The electronic architecture lends itself readily to the addition of new interfaces as required (for example, a daughter card). For the data interface, the compressor needs to know how much refrigerant is being consumed by the system. In the context of refrigerators in cryopumps, this can be estimated by the refrigerant flow estimators 210A-n based on combinations of motor speed, T1, T2, Tambient, Psupply, Preturn and a number of constants defined for a specific cryopump refrigerator. Alternatively, the mass flow control algorithms estimate the refrigerant consumption based on data returned from the cryopump refrigerators. As an example, a compressor is enabled to control refrigerant supply directly to refrigerators in OnBoard® IS. OnBoard® and P300 cryopump refrigerators may also be controlled by accessing T1 and T2 temperatures via Gold Link, the Network Interface Terminal (NIT), or other means. Characterization of other refrigerators and refrigerator/cryopump communications also are used to enable communication, establish refrigerator constants and acquire the necessary operating parameters such as motor speed, T1, T2, and pressures. In addition, the compressor is further enabled to control cryopumps via an Ethernet network. User program settable maps may be used to map in unknown or non-communicating compressors and cryopumps/refrigerators and to establish or obtain operating parameters of refrigerators from host or other performance monitoring systems or have default values.

Figure 7:
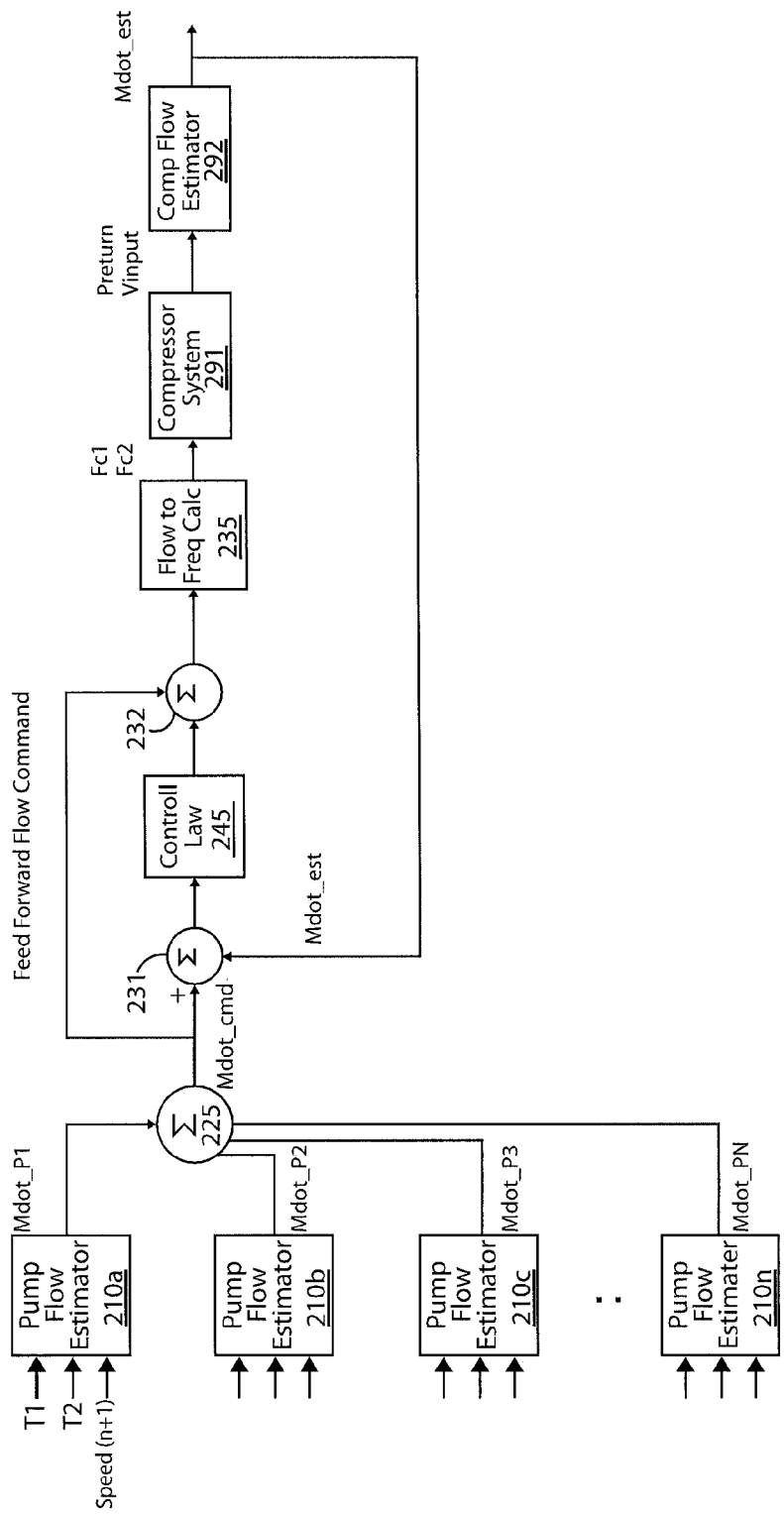
FIG. 7 is a block diagram of a refrigeration system for controlling supply of a refrigerant.

FIG. 7 shows a block diagram of a refrigeration system for controlling a supply of a refrigerant as described above. For instance, FIG. 7 illustrates, as described above. the method and corresponding refrigeration system for enabling a compressor, with mass flow control, to interface with any system utilizing a gas phase refrigerant such as helium.

Adaptive Power Management of Variable Speed Compressors

A maximum speed for the compressor is established to protect the compressor from operating in an over-current condition. Typical existing over-current protection is to protect primarily against short term over-current conditions. The first level of over-current protection is the current glitch circuit which protects from cross-conduction type current spikes, i.e., very large currents occurring over a few microseconds (in this case, the detection and shut off both occur in hardware). This current level is usually determined by the max pulse current of the power devices. The next level of over-current protection comes in the software which protects against thermal faults induced by over-current. This is slower than the glitch but is still quite fast. But there is still a significant gap between this short term thermal over-current and the continuous running current. The continuous current limit is currently held by simply estimating the max speed the motor can run at based only on DC bus voltage. Alternatively, current feedback may be used to limit the speed such that the compressor doesn't exceed the current limit. When the compressor relies on an estimate of the maximum speed based on the DC bus voltage only, it uses the standard operating supply and return pressures for the system. In high pressure Gifford McMahon refrigeration systems the pressures are 400 psig supply and 200 psig return. However, the values may be user programmable. The use of standard operating supply and return pressures, generally, is a good assumption when operating in closed loop (active) mode, however this is not a valid assumption when operating in fixed speed mode. In an alternative control method, calculations of maximum operating speed based differential pressure, compressor characteristics, and upper limit thresholds are used to reduce the motor speed to protect the compressor from an overcurrent condition. An additional control method to limit current may include use of return pressure in the calculations of maximum allowed speed alone or in combination with the differential pressure calculation above which the operating speed will be reduced to reduce the current of the compressor.

If the correction due to current feedback exceeds a threshold (e.g., 5 Hz), then a warning flag will be set to indicate "excessive speed reduction due to over-current." So the compressor will continue to operate at reduced speed but will provide a warning that indicates that speed was reduced to prevent an over-current condition.

A method relates to controlling maximum power dissipation in a compressor motor windings as well as to limit maximum current allowed by driver circuits. Control of the maximum power and current is important to prevent overheating of the motors as well as to prevent damage to the driver circuits and connectors. This power management must be adaptive, where it can compensate for changes in operating pressures and DC bus voltages, as well as changes in motor current.

Because current and power are a function of motor speed, motor speed is used to limit current and power. Maximum speed of compressor motors are therefore determined based on the maximum allowed continuous running current and maximum power dissipated in the compressor. While operating in fixed speed mode, max motor speed is estimated based on DCbus voltage, differential pressure and return pressure. Higher DCbus voltages yield higher maximum motor speed, while higher differential pressure or higher return pressure yield lower max speeds. The compressor controller must provide an immediate reduction in maximum speed in the event that a high return or differential pressure exists, to eliminate ramping to a high current. In active mode, maximum speed is determined based on DCbus voltage, expecting that the closed loop reponse will take care of large pressure offsets. And finally, in either active for fixed speed mode, anytime the max current of the two motors exceeds the max continuous running current, the max speed will be reduced at a slow rate such as 0.6 Hz/minute until the overcurrent situation is rectified. The motor current may be measured directly. If the "max speed correction due to motor overcurrent" exceeds a total of preset value such 5 Hz, a warning will be issued to notify the host that there has been significant speed reduction to accommodate an over-current situation. At all times, a hardware over-current fault is in place to shut motors down in the event of a peak current exceeding the max pulse current of the power device.

Therefore, motor speed is reduced anytime there is excessive motor current. Similarly, max motor speed is increased any time that the motor is being commanded to run at max speed and simultaneously the max current of the two motors is below a threshold value. The max motor speed is then increased at a slow rate such as 0.6 Hz/minute, until the undercurrent condition is rectified. And finally, there is another max motor speed correction made anytime the maximum speed correction due to motor overcurrent is greater than zero: which implies that the estimated max motor speed has been reduced due to over-current. In this case, a very slow drift is always applied, such as of 0.03 Hz/minute, to the maximum motor speed until the over-current protection is zero. This prevents the stackup of startup transients over long periods of time from producing low max speeds.

Additionally, passive and active power factor correction may be used for three phase variable speed compressors.

Compressor Control Strategy for Minimizing Low Frequency Vibration

Vibration and sound control are very important in vacuum system design, especially for compressors. Vibration may result in adverse effects both on the compressor components and on the surroundings. Excessive vibration can cause parts inside the compressor system to fatigue prematurely, causing a reliability problem. Vibration can affect the surroundings in two ways, first as audible noise and secondly as vibration transmitted through any physical connection, such as the floor and external tubing connections. All rotating machinery will generate harmonics of its rotational frequencies, with the fundamental being the strongest component by far; vibration resulting from these harmonics must be controlled, but this implies that you don't have to worry about vibration below the fundamental frequency. However, when combining multiple compression pumps into a single compressor system, the beat frequencies (half the difference frequency) of the various pumps produce sub harmonic vibration that can often be objectionable and is much more difficult to attenuate. The following addresses this issue.

In a single compressor system that has a multitude of mechanical compression pumps, the many pumps may be controlled to act as a single unit. Rotational frequencies that are not of the same value can cause vibration at subharmonic beat frequencies, now greatly increasing the range of frequencies over which to control vibration. To eliminate this difficulty, control of the individual pumps must be such that all pumps are operating at the same input frequency (actual operating frequencies vary slightly due to slip variations from motor to motor). The control scheme ensures that all pumps operate from the same PWM frequency by providing the same PWM signal to all pumps within the system.

Variable Cooling for Variable Speed Compressors

Variable speed compressors produce varying amounts of heat over the range of operating speeds. Higher operating speeds produce more heat and require more cooling. Cooling water flow to meet the high demand of high speed operation will result in wasted cooling water flow at low speed operating conditions. A method and corresponding refrigeration system relate to minimizing cooling water used by the compressors through the use of thermostatic valves in the cooling circuits.

Thermostatic valves placed in the cooling water circuit at the outlet of the compressor or group of compressors or in the individual cooling circuits within the compressor may reduce the total cooling water flow by the devices. The temperature setpoint of the valves will maintain the items being cooled at safe levels for performance and reliability. These valves may be place in circuits for cooling counterflow heat exchangers for cooling fluids such as the refrigerants and lubricating fluid as well as heat exchangers attached to the compressor pump and electronics cooling plates. Additionally, the use of thermostatic valves on the entrance or exit to electronics cooling plates is to maintain the cooling plate for the electronics above a threshold to prevent condensation. Thermally isolated thermostatic flow control valves may be coupled to the cooling water circuit to adjust flow around a temperature setpoint, thereby maintaining a minimum amount of cooling water necessary to maintain motor winding temperatures within operating specifications. The thermostatic valves may be passive wax valves set to the appropriate threshold. Alternative embodiments rely on active, electro-mechanical control methods that inherently reduce reliability, increase energy consumption, and reduce cost. These include the use of pulsed solenoid valves to dynamically control water flow. A water filter may be applied at the input.

Fault Detection and Recovery

A method and corresponding refrigeration system relate to fault detection and recovery. For example, refrigeration systems as described above may be modified to monitor trends in compressor max motor currents to help predict onset of motor failure, add accelerometers to compressor and pump motors to help characterize bearing damage, monitor trends in $2^{nd}$ stage heater data to characterize $2^{nd}$ stage wear, and monitor cool down data to help predict pump issues such as leaks.

A failure that shuts down a vacuum system (compressor and pumps) can interfere with system processing, and may result in expensive tool down time of semiconductor fab equipment. By implementing fault tolerance and system diagnostics, and by automating system recovery, a compressor has been configured to protect itself from damage, reduce the risk of failure, and prevent unscheduled down time.

Embodiments of the present invention enable compressors and cryopumps to constantly monitor a number of input signals including currents, voltages, pressures, water temperature, $1^{st}$ and $2^{nd}$ stage pump temperatures, compressor and cryopump speeds etc., in order to report unfavorable operating conditions. When an undesirable condition occurs, the entire system coordinates actions so as to minimize the impact of the offending condition. The course of action can range anywhere from a user warning message with no loss of performance to loss of a single compressor motor forcing the system to run at derated capacity to complete the process. However, compressor or cryopump shut down is considered the absolute last resort, and only done when no other options are possible.

Warnings are used to alert a user of an undesirable condition such as a low differential pressure or low AC input voltage. In this state, the system will continue to function at near full capacity. If the warning is temporary, it may notify the user of a possible issue with facilities such as input power. If the cause of the warning is unknown and persistent, the user will know to schedule maintenance before a fault results.

Faults are more serious and will generally result in the shutdown of a pump or cryo motor with resulting loss of system performance. For example, for a compressor with two compressor pumps, when one motor is faulted, the second motor is ramped up to its maximum speed to provide as much refrigerant as possible to compensate. Helium manager 220 then attempts to adapt the system to a reduced helium allocation. Although the max capacity of the system is cut in half, this is often sufficient to complete the process until maintenance can be scheduled.

Fault recovery is a means of making the best of the faults that you have. At the lowest level of fault recovery, after a fault has caused a motor shut down, the fault continues to be monitored and when it is cleared, the motor will be restarted, in the hope that the fault was caused by a transient condition that is not likely to be repeated. To prevent constant cycling between faults and retries, a motor will be permanently latched off if a specified number of faults occurs within a certain period of time. An example of fault recovery at a higher level is the action taken by Helium manager 220 to adjust cryopump speeds down in an attempt to allow the system to operate with less helium.

A system log may be used to capture and record each warning and fault event, thereby providing additional diagnostic capability and post mortem failure analysis.

Embodiments of the present invention utilize a hierarchical approach where faults are detected and actions are taken at various levels in a refrigeration system architecture. Faults are divided into two general categories, those which involve a single component (compressor or cryopump) and those which involve the entire vacuum system. For example, an over-current or over-temperature fault from a compressor or cryopump refrigerator motor will affect that motor only and may result in the loss of that component. On the other hand, the loss of helium differential pressure is a fault that can result in the loss of functionality of the entire system. Faults are further broken down into faults and warnings, where warnings are used to provide notification of a potential problem which may not require immediate action. The various levels at which faults are detected and where action is taken indicates where you are in a control hierarchy. The more time critical faults are usually handled at the lower levels where direct and immediate response is important.

Example Fault detection levels are as follows:

Level 0: Hardware level, hardware responds directly to a fault, while providing fault information to the processors (e.g., gfi fault, motor over current fault).

Level 1: Embedded microcontroller/DSP level, where DSP detects and responds to a fault (e.g., motor thermal fault). Most compressor and cryo issues are detected at this level and a certain amount of fault recovery is attempted at this level.

Level 2: Application and communication processor level (e.g., ARM 9) faults usually imply a fault with the board's hardware which can range from a memory issue to a problem with one of the many communications interfaces. Fault recovery for the compressors and cryos is often done at this level where the processor tries to recover from a Level 0 or Level 1 fault, sometimes by simply doing retries.

Level 3: This is the System Controller process level where this process can take advantage of complete system knowledge to assist in fault recovery. For example, if one of the pressure sensors is faulty and indicates that differential pressure has collapsed below 50 psi, then at level 2, the system would be told to shut down, however, at level 3, if the pumps indicate that they are maintaining temperature, then there's no reason to shut down and a very expensive shutdown has simply turned into a maintenance visit to replace the pressure sensor.

Table 1 below illustrates examples of the hierarchical fault detection and recovery approach for a compressor. The table entries list various fault actions depending on the particular fault type and fault action level. Actions range from detection to attempts at recovery.

TABLE 1

| | Fault Action Fault Type | | | | | | |
|---|---|---|---|---|---|---|---|
| | Comp Motor 1 | | | | Comp Motor 2 | | |
| Level | Over-current | Over temp IGBT | Motor over-temp | Heat exchanger over-temp | Over-current | Over temp IGBT | Motor over-temp |
| Level 0 H/W | Shut M1 Off | — | — | — | Shut M2 Off | — | — |
| Level 1 DSP | Send to Applic. Proc | Shut M1 Off | Shut M1 Off | Shut M1 Off | Send to Applic. Proc | Shut M2 Off | Shut M2 Off |
| Level 2 Applic. And Comm. Proc. | 3 Retries in 1 hour Latch off Pass fault to Controller Process | 3 Retries in 1 hour Latch off Pass fault to Controller Process | 3 Retries in 1 hour Latch off Pass fault to Controller Process | 3 Retries in 1 hour Latch off Pass fault to Controller Process | 3 Retries in 1 hour Latch off Pass fault to Controller Process | 3 Retries in 1 hour Latch off Pass fault to Controller Process | 3 Retries in 1 hour Latch off Pass fault to Controller Process |
| Level 2 Applic. And Comm. Proc. | 3 Retries in 1 hour Latch off Pass fault to Controller Process | 3 Retries in 1 hour Latch off Pass fault to Controller Process | 3 Retries in 1 hour Latch off Pass fault to Controller Process | 3 Retries in 1 hour Latch off Pass fault to Controller Process | 3 Retries in 1 hour Latch off Pass fault to Controller Process | 3 Retries in 1 hour Latch off Pass fault to Controller Process | 3 Retries in 1 hour Latch off Pass fault to Controller Process |
| Level 3 Controller Process | Pass fault to host | Pass fault to host | Pass fault to host | Pass fault to host | Pass fault to host | Pass fault to host | Pass fault to host |

| | Fault Action Fault Type | | | |
|---|---|---|---|---|
| | Comp Motor 2 | System | | |
| Level | Heat exchanger over-temp | Loss of 24 Volts | Loss of Pressure Sensors | Loss of DeltaP |
| Level 0 H/W | — | — | — | — |
| Level 1 DSP | Shut M2 Off | Shut M1 & M2 off | Warning issued to Applic. Proc | If valid Pressures M1&M2 off If Active & when motor turn off: Both motors stay on |
| Level 2 Applic. And Comm. Proc. | 3 Retries in 1 hour Latch off Pass fault to Controller Process | 3 Retries in 1 hour Latch off Pass fault to Controller Process | Pass warning to CAP | 3 Retries in 1 hour Latch off |
| Level 2 Applic. | 3 Retries in 1 hour | 3 Retries in 1 hour | Pass warning to CAP | 3 Retries in 1 hour Latch off |

TABLE 1-continued

| | | | |
|---|---|---|---|
| And Comm. Proc. | Latch off Pass fault to Controller Process | Latch off Pass fault to Controller Process | |
| Level 3 Controller Process | Pass fault to host | Pass fault to host | Pass warning to host, Pass fault to host then by monitoring pumps, determine if pressures are sufficient to continue to run comps at full speed |

In an alternative embodiment, a detection of a fault type of a motor reaching a maximum temperature threshold (e.g., over-temp) condition may cause a controller to gradually reduce the speed of the motor until the motor (e.g. compressor) reaches a minimum speed threshold. Faults may be stored within a fault detection device or may be issued as a warning to other system components.

Table 2 below illustrates examples of the hierarchical fault detection and recovery approach for a cryopump. The table entries list various fault actions depending on the particular fault type and fault action level. Actions range from detection to attempts at recovery.

TABLE 2

| | Fault Action Fault Type | | | | | |
|---|---|---|---|---|---|---|
| | Cryopump Motor | | | System | | |
| | | | | | Excessive motor | |
| Level | Over-current | Motor over-temp | Heaters HFI Trip | Loss of Comm DSP to Applic Processor | speed to reach T2 setpoint | Loss of DeltaP |
| Level 0 H/W | Shut Motor Off | — | Shut Heaters Off | — | — | — |
| Level 1 DSP | Send fault to Applic. Proc. | Shut Motor Off Send fault to Applic. Proc. | Send fault to Applic. Proc. | Shut Pump down, by disabling heaters, TC gauge, and reseting valve states, valve sequencing depends on whether PVD, Implant | Continue to increase 1$^{st}$ stage motor speed as required while issuing warning to Application Processor | Shut Pump down, by disabling heaters, TC gauge, and reseting valve states, valve sequencing depends on whether PVD, Implant |
| Level 2 Applic. And Comm. Proc. | 3 Retries in 1 hour Latch off Pass fault to Controller Process | 3 Retries in 1 hour Latch off Pass fault to Controller Process | 3 Retries in 1 hour Latch off Pass fault to Controller Process | Report lost of Comm fault to Controller Process | Pass warning to Controller Process | Report lost of Comm fault to Controller Process |
| Level 3 Controller Process | Pass fault to host | Pass fault to host | Pass fault to host | Pass fault to host | Pass warning to host, reporting a problem with the 2$^{nd}$ stage maintaining temperature | Pass fault to host |

Table 1 and Table 1 list various fault actions depending on the particular fault type and fault action level for a refrigerator system. Actions range from detection to attempts at recovery. In certain scenarios, a fault in a refrigeration system may cause communication losses in the system. Thus, in order to prevent a scenario of an inadequate supply of refrigerant, embodiments of the present invention turn on all compressors and set the speed of all the compressors to a maximum speed.

While example embodiments have been particularly shown and described, it will be understood by those skilled in the art that various changes in form and details may be made therein without departing from the scope of the embodiments encompassed by the appended claims.

What is claimed is:

1. In a cryogenic refrigeration system in which plural compressors, controlled by a controller, supply helium refrigerant at a supply pressure to plural cryogenic refrigerators, each comprising a reciprocating displacer, that expand the helium refrigerant to absorb heat to produce a cooling effect and that return the helium refrigerant to the plural compressors at a return pressure, a method for controlling supply of the helium refrigerant, the method comprising:

at the controller, receiving communication from the plural cryogenic refrigerators indicating demand for helium refrigerant;

determining an aggregated demand for the helium refrigerant for the plural cryogenic refrigerators;

sensing supply pressure from the plural compressors;

sensing return pressure to the plural compressors;

at the controller, calculating a helium refrigerant supply correction based on a difference between sensed supply pressure and sensed return pressure;

computing amount of helium refrigerant to supply to the plural cryogenic refrigerators based on the aggregated demand for the helium refrigerant corrected by the helium refrigerant supply correction; and with the controller, controlling speed of at least one of the plural compressors that delivers helium refrigerant to the plural cryogenic refrigerators to deliver the computed amount of helium refrigerant.

2. The method of claim 1, further comprising selectively turning the plural compressors on or off to deliver the computed amount of refrigerant.

3. The method of claim 1, further comprising turning the plural compressors on or off to deliver the computed amount of helium refrigerant and selecting specific compressors to be turned on or off based on a history of turn on and offs of the plural compressors.

4. The method as claimed in claim 1 wherein the at least one of the plural compressors includes at least one fixed speed compressor and at least one variable speed compressor.

5. The method as claimed in claim 1 wherein the plural cryogenic refrigerators are included in cryopumps.

6. A cryogenic refrigeration system for controlling supply of helium refrigerant, the system comprising:
   at least one compressor, the at least one compressor including a high pressure supply line and a low pressure return line, the at least one compressor supplying helium refrigerant;
   a plurality of cryogenic refrigerators, each comprising a reciprocating displacer, coupled to the at least one compressor to receive helium refrigerant from the supply line and return helium refrigerant to the return lines;
   a supply pressure sensor sensing supply pressure on the supply line;
   a return pressure sensor sensing return pressure on the return line;
   a system controller including:
      a helium refrigerant management system that receives communications from the plurality of cryogenic refrigerators, indicating demand for helium refrigerant and that determines an aggregated demand for the helium refrigerant for the plural cryogenic refrigerators; and
      a helium refrigerant supply correction controller that calculates a helium refrigerant supply correction based on a difference between sensed supply pressure and sensed return pressure and that computes amount of helium refrigerant to supply to the cryogenic refrigerators, based on the aggregated demand for the helium refrigerant corrected by the helium refrigerant supply correction; and
      a compressor controller that controls speed of the at least one compressor that delivers helium refrigerant to the plural cryogenic refrigerators to deliver the computed amount of helium refrigerant.

7. The cryogenic refrigeration system as claimed in claim 6 wherein the compressor controller turns the at least one compressor on or off to deliver the computed amount of helium refrigerant.

8. The cryogenic refrigeration system as claimed in claim 6 wherein the compressor controller turns variable speed compressors of the at least one compressor on or off to deliver the computed amount of helium refrigerant and selects specific variable speed compressors of the at least one compressor to be turned on or off based on a history of turn on and offs of the variable speed compressors of the at least one compressor.

9. The cryogenic refrigeration system as claimed in claim 6 wherein the cryogenic refrigerators are associated with respective cryopumps.

10. The system as claimed in claim 6 wherein the compressor controller switches to a dual variable speed compressor operational state by turning one of two variable speed compressors of the at least one compressor on if a calculated amount of helium refrigerant to supply to plural cryogenic refrigerators is greater than a threshold helium refrigerant output of a single compressor of the at least one compressor for a period of time.

11. A method for controlling supply of a refrigerant, the method comprising:
   at a controller, obtaining an aggregated demand for a helium refrigerant based on communications from plural cryogenic refrigerators, each comprising a reciprocating displacer; and
   with the controller, controlling speed of a compressor of a plurality of compressors that deliver gas refrigerant to the plural cryogenic refrigerators, based on the aggregated demand for the refrigerant corrected by a refrigerant correction metric calculated based on supply and return refrigerant pressure; and
   turning a subset of the plurality of compressors on or off based on the aggregated demand for the refrigerant corrected by the refrigerant correction metric.

12. The method as claimed in claim 11 wherein the plurality of compressors includes at least one fixed speed compressor and at least one variable speed compressor.

13. The method as claimed in claim 11 wherein the cryogenic refrigerators are included in cryopumps.

14. A refrigeration system for controlling supply of a refrigerant, the system comprising:
   a compressor of a plurality of compressors, the compressor of the plurality of compressors including a high pressure supply line and a low pressure return line, the compressor of the plurality of compressors configured to supply a helium refrigerant;
   a plurality of cryogenic refrigerators, each comprising a reciprocating displacer, coupled to the compressor of the plurality of compressors to receive helium refrigerant from the supply line and return helium refrigerant to the return lines; and
   an electronic controller configured to obtain an aggregated demand for the helium refrigerant based on communications from the plurality of cryogenic refrigerators, the electronic controller further configured to control speed of the compressor of the plurality of compressors based on the aggregated demand for the refrigerant corrected by a refrigerant correction metric, the correction metric determined based on a supply pressure feedback loop from the high pressure supply line and a return pressure feedback loop from the low pressure return line, the electronic controller being configured to turn a subset of the plurality of compressors that supply the helium refrigerant to the refrigerators on or off based on the aggregated demand for the refrigerant corrected by the refrigerant correction metric.

15. The refrigeration system as claimed in claim 14 wherein the plurality of compressors comprise a plurality of variable speed compressors.

16. The refrigeration system as claimed in claim 14 wherein the plurality of compressors comprise at least one variable speed compressor and at least one fixed speed compressor.

17. The refrigeration system as claimed in claim 14 wherein the cryogenic refrigerators are associated with respective cryopumps.

18. The system as claimed in claim 14 wherein the electronic controller is further configured to select one of two variable speed compressors of the plurality of compressors to turn off based on a history of turn offs.

* * * * *